United States Patent [19]

Hayashi et al.

[11] 4,165,437
[45] Aug. 21, 1979

[54] Δ³-PROSTAGLANDIN ANALOGS

[75] Inventors: Masaki Hayashi; Seiji Kori, both of Takatsuki; Yoshinobu Arai, Toyonaka; Takanori Okada, Osaka; Yoshitaka Konishi, Takatsuki, all of Japan

[73] Assignee: Ono Pharmaceutical Company, Ltd., Osaka, Japan

[21] Appl. No.: 934,444

[22] Filed: Aug. 17, 1978

Related U.S. Application Data

[62] Division of Ser. No. 774,828, Mar. 7, 1977.

[30] Foreign Application Priority Data

Mar. 12, 1976 [GB] United Kingdom ............... 10118/76
Aug. 9, 1976 [GB] United Kingdom ............... 33154/76

[51] Int. Cl.² .................................... C07C 177/00
[52] U.S. Cl. ..................................... 560/121; 562/503
[58] Field of Search ...................... 560/121; 562/503

[56] References Cited

U.S. PATENT DOCUMENTS 3,931,296   1/1976   Hayashi et al. ................. 260/514

Primary Examiner—Robert Gerstl
Attorney, Agent, or Firm—Frank S. Chow; Albert H. Graddis

[57] ABSTRACT

The present invention relates to prostaglandin analogues of the general formula:

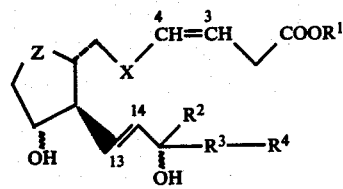

[wherein X represents cis or trans-vinylene or ethylene, R represents

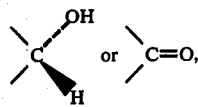

$R^1$ represents a hydrogen atom or a straight- or branched-chain alkyl group containing from 1 to 12 carbon atoms, $R^2$ represents a hydrogen atom or a methyl group, $R^3$ represents a straight- or branched-chain alkylene group containing from 1 to 7 carbon atoms and $R^4$ represents a cycloalkyl group containing from 5 to 7 carbon atoms, a grouping of the formula:

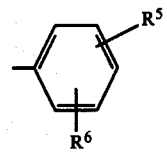

(wherein $R^5$ and $R^6$, which may be the same or different, each represent a hydrogen atom or halogen atom, a trifluoromethyl group or a straight- or branched-chain alkyl group containing from 1 to 4 carbon atoms), or a grouping of the formula:

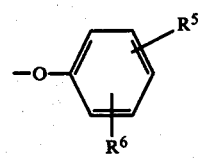

(wherein $R^5$ and $R^6$ are as hereinbefore defined), or $R^3$ and $R^4$ together represent a straight- or branched-chain alkyl group containing from 1 to 10 carbon atoms, and (1) the double bond between $C_3$-$C_4$ is trans or cis, or trans and cis, when X is cis-vinylene or ethylene, and (2) the double bond between $C_3$-$C_4$ is trans, when X is trans-vinylene, and the double bond between $C_{13}$-$C_{14}$ is trans] and cyclodextrin clathrates of such acids and esters, and when $R^1$ represents a hydrogen atom, non-toxic salts thereof, which exhibit characteristic prostaglandin-like activities.

7 Claims, No Drawings

Δ³-PROSTAGLANDIN ANALOGS

This is a division of application Ser. No. 774,828 filed Mar. 7, 1977.

This invention is concerned with new prostaglandin analogues.

Prostaglandins are derivatives of prostanoic acid which has the following formula:

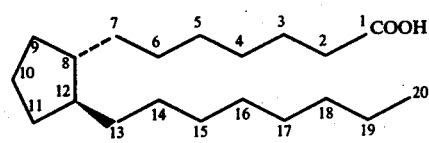

Various types of prostaglandins are known, the types depending inter alia on the structure and substituents on the alicyclic ring. For example, the alicyclic rings of prostaglandins F(PGF) and E(PGE) have the structures:

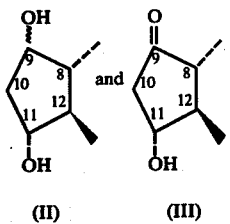

respectively. In the foregoing formulae and in other formulae throughout this specification the dotted lines denote, in accordance with generally accepted rules of nomenclature, that the attached grouping lies behind the general plane of the ring system, i.e. that the grouping is in α-configuration, the thickened lines ▶ denote that the grouping lies in front of the general plane of the system, i.e. that the grouping is in β-configuration, and the wavy line ∼ indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$-$C_{14}$(trans-$\Delta^{13}$) and $PG_2$ compounds have a cis-double bond between $C_5$-$C_6$ and a trans-double bond between $C_{13}$-$C_{14}$(cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures IV and V.

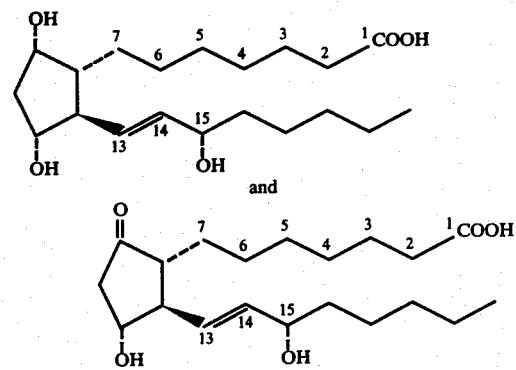

respectively. The structures of $PGF_{2\alpha}$ and $PGE_2$, as members of the $PG_2$ group correspond to those of formulae IV and V respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin $F_{1\alpha}$ (dihydro-$PGF_{1\alpha}$) and dihydro-prostaglandin $E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as homo-prostaglandins (methylene group added) or nor-prostaglandins (methylene group eliminated), and, when more than one methylene group is added or eliminated, the number is indicated by di- tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid separation, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs have vasodilator and diuretic activities. PGEs are useful for improvement in patients suffering from cerebral vascular disease because they increase the cerebral blood flow and are also useful in the treatment of asthmatic conditions in patients because of their bronchodilating activity.

During the past decade widespread investigations have been carried out in order to discover inter alia new products possessing the pharmacological properties of the "natural" prostaglandins or one or more of such properties to an enhanced degree, or hitherto unknown pharmacological properties. It has now been found that by introducing a double bond between the carbon atoms in the 3- and 4- positions of prostaglandins $F_{2\alpha}$ and $E_2$ and certain analogues thereof, the pharmacological properties of the "natural" prostaglandins are, in some aspects of their activities, improved or modified.

The present invention accordingly provides new prostaglandin analogues of the general formula:

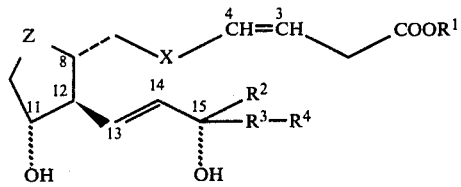 (VI)

[wherein X represents cis or trans-vinylene (i.e. —CH=CH—). or ethylene (i.e. —CH$_2$CH$_2$—), Z represents

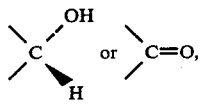

R$^1$ represents a hydrogen atom or a straight- or branched-chain alkyl group containing from 1 to 12 (preferably 1 to 4) carbon atoms, R$^2$ represents a methyl group or, preferably, a hydrogen atom, R$^3$ represents a straight- or branched-chain alkylene group containing from 1 to 7 (preferably 1 or 2) carbon atoms and R$^4$ represents a cycloalkyl group containing from 5 to 7 carbon atoms, a grouping of the formula:

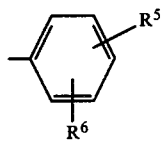 (VII)

(wherein R$^5$ and R$^6$, which may be the same or different, each represent a hydrogen atom or halogen atom, a trifluoromethyl group or a straight- or branched-chain alkyl group containing from 1 to 4 carbon atoms), or a grouping of the formula:

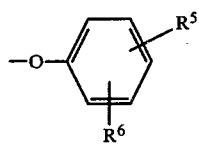 (VIII)

(wherein R$^5$ and R$^6$ are as hereinbefore defined), or R$^3$ and R$^4$ together represent a straight- or branched-chain alkyl group containing from 1 to 10 carbon atoms, and (1) the double bond between C$_3$-C$_4$ is trans or cis, or trans and cis, when X is cis-vinylene or ethylene and (2) the double bond between C$_3$-C$_4$ is trans, when X is trans-vinylene, and the double bond between C$_{13}$-C$_{14}$ is trans] and cyclodextrin clathrates of such acids and esters, and when R$^1$ represents a hydrogen atom, non-toxic (e.g. sodium) salts thereof.

It is to be understood that in subsequent formulae appearing in this specificatiion the C$_{13}$-C$_{14}$ double bond is trans.

Preferred compounds of general formula VI are those wherein R$^1$ represents a hydrogen atom or a methyl group; preferably R$^2$ represents a hydrogen atom, preferably R$^3$ represents methylene (i.e. —CH$_2$—) or ethylene, preferably R$^4$ represents a grouping of formula VII or VIII in which R$^5$ preferably represents a hydrogen atom and R$^6$ preferably represents a hydrogen atom or a chlorine atom or a trifluoromethyl group, or preferably R$^3$ and R$^4$ together represent a pentyl or 1,1-dimethylpentyl group, and preferably the hydroxy groups depicted in formula VI in α- or β-configuration are attached to the carbon atom in α-configuration.

The present invention is concerned with all compounds of general formula VI in the "natural" form or its enantiomeric form, or mixtures thereof, more particularly the racemic form consisting of equimolecular mixtures of natural and its enantiomeric form.

As will be apparent to those skilled in the art, the compounds depicted in general formula VI have at least four centres of chirality, these four centres of chirality being at the alicyclic ring carbon atoms identified as 8, 11 and 12 and at the C-15 carbon atom which has attached to it a hydroxy group. A further centre of chirality occurs when the symbol Z represents

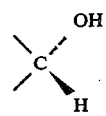

and further centres of chirality may occur in groups represented by the symbols R$^1$, R$^3$ and R$^4$. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have a hydroxy group as depicted in the 15-position are to be considered within the scope of general formula VI.

According to a feature of the present invention, the prostaglandin analogues of general formula VI, wherein X represents cis-vinylene or ethylene, R$^1$ represents a hydrogen atom or a straight- or branched-chain alkyl group containing from 1 to 4 carbon atoms and the other symbols are as hereinbefore defined, i.e. compounds of the general formula:

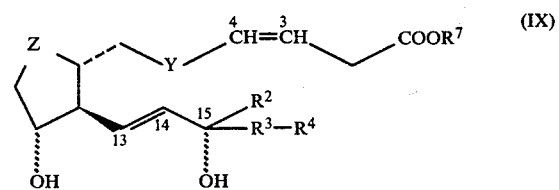 (IX)

(wherein Y represents cis-vinylene or ethylene, R$^7$ represents a hydrogen atom or a straight- or branched-chain alkyl group containing from 1 to 4 carbon atoms, preferably a methyl group, the other symbols are as hereinbefore defined and the double bond between C$_3$-C$_4$ is trans or cis, or trans and cis) are prepared by the process which comprises hydrolysing a cyclopentane derivative of the general formula:

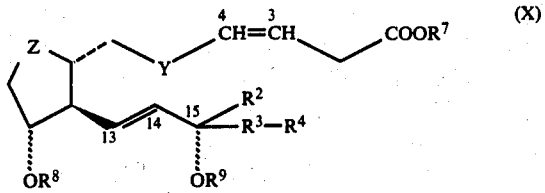

(wherein R⁸ represents a 2-tetrahydrofuranyl group or a 1-ethoxyethyl group or a 2-tetrahydropyranyl group unsubstituted or substituted by at least one alkyl group, R⁹ represents a hydrogen atom or a 2-tetrahydrofuranyl group or a 1-ethoxyethyl group or a 2-tetrahydropyranyl group unsubstituted or substituted by at least one alkyl group, R⁹ being other than hydrogen when Z represents

the other symbols are as hereinbefore defined and the double bond between C₃-C₄ is trans or cis, or trans and cis) to convert to a hydroxy group the group OR⁸ and, when R⁹ is other than a hydrogen atom, the group OR⁹ to obtain a PGF or PGE compound of general formula IX.

It is to be understood that in subsequent formulae appearing in this specificatiion the double bond between C₃-C₄ in the grouping

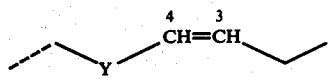

attached to the cyclopentane ring is as specified above in relation to compounds of general formulae IX and X.

The groups OR⁸ and OR⁹ (when R⁹ is other than a hydrogen atom) of compounds of general formula X (preferably such groups are 2-tetrahydropyranyl) may be converted to hydroxy groups by mild hydrolysis (1) with an aqueous solution of an organic acid such as acetic acid, propionic acid, oxalic acid, or p-toluenesulphonic acid, or an aqueous solution of an inorganic acid such as hydrochloric acid or sulphuric acid, advantageously in the presence of an inert organic solvant miscible with water, e.g. a lower alkanol such as methanol or ethanol, preferably methanol, or an ether such as dimethoxyethane, dioxan, or tetrahydrofuran, preferably tetrahydrofuran, at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° to 45° C. Advantageously the mild hydrolysis may be carried out with a mixture of hydrochloric acid, water and tetrahydrofuran or methanol, a mixture of acetic acid, water and tetrahydrofuran, or a mixture of p-toluenesulphonic acid and methanol. The products of general formula IX may be purified by column chromatography on silica gel, which procedure may, when the starting material of general formula X is a mixture of compounds with the group OR⁹ in the 15-position in α- and β-configuration, lead to a separation of the resulting 15α-hydroxy and 15β-hydroxy isomers of general formula IX.

The products of general formula IX may be separated by thin layer chromatography on silica gel pre-treated with silver nitrate using an inert organic solvent medium, e.g. chloroform and methanol, or chloroform and ethanol, as developing solvent to give the trans-Δ³ and cis-Δ³ prostaglandin analogues of general formula IX.

Compounds of general formula X, wherein R⁸ and R⁹ each represent a 2-tetrahydrofuranyl group or a 1-ethoxyethyl group or a 2-tetrahydropyranyl group unsubstituted or substituted by at least one alkyl group and Z represents

[hereafter depicted in general formula XB], may be prepared from compounds of general formula X, wherein R⁸ and R⁹ each represent a 2-tetrahydrofuranyl group or a 1-ethoxyethyl group or a 2-tetrahydropyranyl group unsubstituted or substituted by at least one alkyl group and Z represents

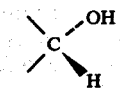

by methods known per se for the conversion of a hydroxy group in the 9-position of a prostaglandin compound to an oxo group, for example by means of a chromic acid solution (e.g. obtained from chromium trioxide, manganese sulphate and sulphuric acid in water) or Jones' reagent or Collins' reagent or dimethylsulphide—N-chlorosuccinimide complex [cf. J. Amer. Chem. Soc., 94, 7586 (1972)], at a moderately low temperature. By the term "methods known per se" as used in this specification is meant methods heretofore used or described in the chemical literature.

Compounds of general formula X, wherein Z represents

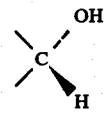

and the other symbols are as hereinbefore defined, i.e. compounds of the general formula:

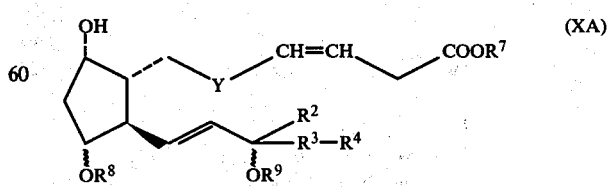

(wherein the various symbols are as hereinbefore defined) may be prepared from compounds of the general formula:

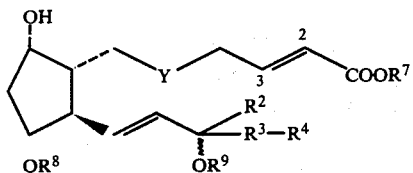
(XI)

(wherein the various symbols are as hereinbefore defined, and the double bond between $C_2$-$C_3$ is trans) by (i) reaction with an alkali metal, e.g. sodium or potassium, hydroxide or carbonate in the presence of an inert organic solvent, e.g. an alkanol containing from 1 to 4 carbon atoms, e.g. methanol or ethanol, at a temperature ranging from ambient to $-20°$ C., or (ii) reaction with equimolecular quantities of a lithium compound of the general formula:

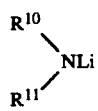
(XII)

(wherein $R^{10}$ and $R^{11}$, which may be the same or different, each represent a straight- or branched-chain alkyl group containing from 1 to 6 carbon atoms or a cycloalkyl group containing from 3 to 6 carbon atoms), e.g. lithium diisopropylamide, and hexamethylphosphoramide in the presence of an inert organic solvent, e.g. tetrahydrofuran, at a low temperature, e.g. $-70°$ C.

Compounds of general formula IX, wherein Z represents

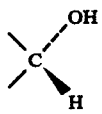

and the other symbols are as hereinbefore defined, i.e. compounds of general formula:

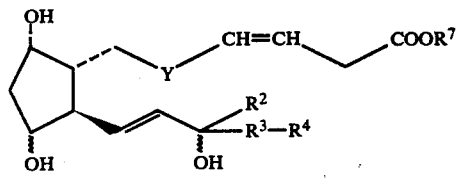
(IXA)

(wherein the various symbols are as hereinbefore defined) are also prepared, according to another feature of the invention, from compounds of the general formula:

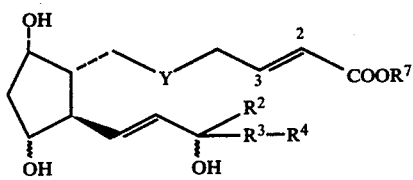
(XIII)

(wherein the various symbols are as hereinbefore defined, and the double bond between $C_2$-$C_3$ is trans) by reaction (i) with an alkali metal, e.g. sodium or potassium, hydroxide or carbonate in the presence of an inert organic solvent, e.g. an alkanol containing from 1 to 4 carbon atoms, e.g. methanol or ethanol, at a temperature ranging from ambient to $-20°$ C., or (ii) with equimolecular quantities of lithium compounds of general formula XII, wherein the various symbols are as hereinbefore defined, e.g. lithium diisopropylamide, and hexamethylphosphoramide in the presence of an inert organic solvent, e.g. tetrahydrofuran, at a low temperature, e.g. at $-70°$ C.

The compounds of formula IXA may be separated by thin layer chromatography on silica gel pre-treated with silver nitrate using an inert organic solvent medium, e.g. chloroform and methanol, or chloroform and ethanol, as developing solvent to give the trans-$\Delta^3$ and cis-$\Delta^3$ prostaglandin analogues of general formula IXA.

Compounds of general formula XIII, wherein the various symbols are as hereinbefore defined, may be prepared from compounds of general formula XI by the procedures hereinbefore described for the conversion of compounds of general formula X into compounds of general formula IX.

Compounds of general formula IX, wherein Z represents

and the other symbols are as hereinbefore defined, i.e. compounds of the general formula:

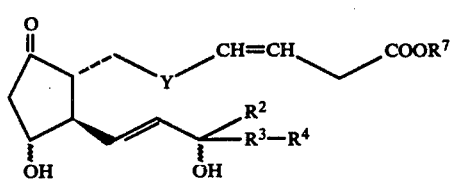
(IXB)

(wherein the various symbols are as hereinbefore defined) are prepared, according to a still further feature of the invention, by the process which comprises hydrolysing the silyloxy groups of a compound of the general formula:

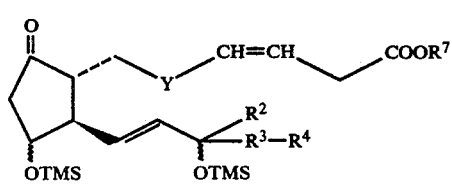
(XIV)

(wherein TMS represents the trimethylsilyl group, and the other symbols are as hereinbefore defined) to hydroxy groups under extremely mild acidic conditions, for example by treatment of a solution of such a compound in an inert organic solvent, e.g. ethyl acetate or diethyl ether, with an aqueous oxalic acid solution, preferably at room temperature.

Compounds of general formula XIV may be prepared by oxidation of compounds of the general formula:

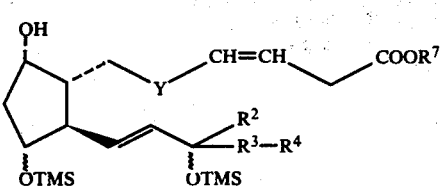

(XV)

(wherein the various symbols are as hereinbefore defined) with Collins' reagent (chromium trioxide-pyridine complex) in the presence of an inert organic solvent, e.g. methylene chloride, preferably at a temperature of about 10° C., or with dimethylsulphide-N-chlorosuccinimide at 0° to −30° C. [cf. E. J. Corey and C. U. Kim, J. Amer. Chem. Soc., 94, 7586 (1972)].

Compounds of general formula XV may be prepared from compounds of general formula IXA by reaction with a suitable trimethylsilylating agent, e.g. N-trimethylsilyldiethylamine or N,O-bis(trimethylsilyl)acetamide, in acetone, preferably at room temperature.

Compounds of general formula XI, wherein the various symbols are as hereinbefore defined, may be prepared by the process which comprises reacting a compound of the general formula:

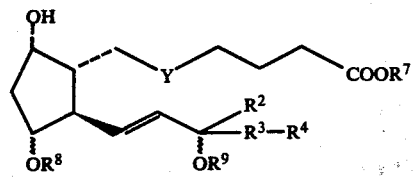

(XVI)

(wherein the various symbols are as hereinbefore defined) with a compound of general formula XII, wherein the various symbols are as hereinbefore defined, to obtain a lithium esterenolate of the general formula:

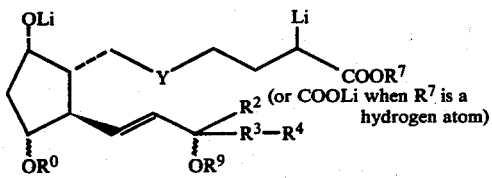

(XVII)

(or OLi when $R^9$ is a hydrogen atom)

(wherein the various symbols are as hereinbefore defined) reacting the lithium esterenolate with benzeneselenenyl bromide (i.e. $C_6H_5SeBr$), or diphenyldiselenide, or a dialkyldisulphide or diphenyldisulphide of general formula $R^{12}SSR^{12}$, wherein $R^{12}$ represents an alkyl group containing from 1 to 4 carbon atoms or a phenyl group, hydrolysing the resulting intermediate to obtain a compound of the general formula:

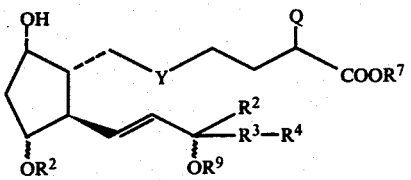

(XVIII)

(wherein Q represents a group —$SeC_6H_5$ or a group —$SR^{12}$, in which $R^{12}$ is as hereinbefore defined, and the other symbols are as hereinbefore defined), treating the resulting compound with hydrogen peroxide or sodium periodate, and decomposing the resulting compound of the general formula:

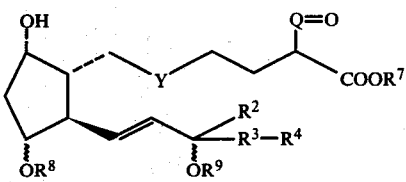

(XIX)

(wherein the various symbols are as hereinbefore defined) to convert the grouping

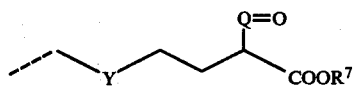

attached to the 8-position of the cyclopentane ring to a trans-$\Delta^2$, grouping

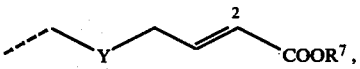

wherein $R^7$ is as hereinbefore defined.

The reaction between compounds of general formula XVI and lithiated amines of general formula XII is carried out in an organic solvent medium, for example, when $R^7$ represents an alkyl group, by adding dropwise a solution of an ester of general formula XVI in tetrahydrofuran to a solution of an amine of general formula XII in tetrahydrofuran at a low temperature, e.g. −78° C., or, when $R^7$ represents a hydrogen atom, adding dropwise a solution of an acid of general formula XVI in tetrahydrofuran to a solution of an amine of general formula XII in tetrahydrofuran at a low temperature in the presence of hexamethylphosphoramide at 0° C., the ratio of the molecular equivalents of compounds of general formula XVI to XII in the reaction mixture being suitably adjusted to obtain a lithium esterenolate of general formula XVII. In the case where a prostaglandin ester is employed as reactant, after completion of the addition of the prostaglandin solution to the amine solution, the reaction mixture is stirred at the same temperature for about 30 minutes to obtain a solution of the lithium esterenolate of general formula XVII. In the case where a prostaglandin acid is employed as reactant ($R^7$ represents a hydrogen atom), the reaction mixture is stirred at room temperature for about 30 minutes to obtain a solution of the lithium esterenolate of general formula XVII.

The reaction between the lithium esterenolate of general formula XVII and benzeneselenenyl bromide, diphenyldiselenide or a dialkyl- or diphenyl-disulphide, is preferably carried out in tetrahydrofuran, hexamethylphosphoramide, diethyl ether, n-hexane or n-pentane or a mixture of two or more of them, tetrahydrofuran being the preferred solvent medium, at a low temperature when $R^7$ in formula XVII represents an alkyl group, e.g. −78° C., or, when $R^7$ in formula XVII represents a hydrogen atom, at 0° C. Thus, to the lithium esterenolate solution obtained as described above there is added a solution in tetrahydrofuran of benzeneselenenyl bromide, diphenyldiselenide or a dialkyl- or diphenyl-disulphide, the temperature of the two solutions being −78° C. or 0° C. according to whether an ester or acid of formula XVII respectively, is the reactant. The reaction mixture is then stirred (when $R^7$ in formula XVII is an alkyl group) at −78° C. (a) for one hour when a selenium compound is the reactant or (b) for 30 minutes when a disulphide is the reactant, and subsequently at ambient temperature, e.g. 15° C. for 30 minutes, or (when $R^7$ in formula XVII is a hydrogen atom) at room temperature for 1 hour 30 minutes. After addition of, for example, a small amount of a saturated aqueous ammonium chloride solution to the solution of the resulting prostaglandin intermediate to hydrolyze it, the product of formula XVIII is extracted with ethyl acetate.

If desired, the intermediate esters of general formula XVIII wherein $R^7$ represents an alkyl group may be converted to corresponding acids of general formula XVIII, i.e. $R^7$ represents a hydrogen atom, by hydrolysis under alkaline conditions. The hydrolysis of the esters under alkaline conditions may be effected with an aqueous solution of an alkali metal, e.g. sodium or potassium, hydroxide or carbonate in the presence of a water-miscible organic solvent, e.g. tetrahydrofuran or an alkanol containing from 1 to 4 carbon atoms, e.g. methanol.

When the product of formula XVIII is a compound wherein Q represents —SEφ, φ representing the phenyl radical, the product is then treated with 5 to 7 molecular equivalents of hydrogen peroxide in a mixture of ethyl acetate and tetrahydrofuran or methanol at a temperature of 30° C. or below, or with 5 molecular equivalents of sodium periodate in the presence of a lower alkanol, preferably methanol, and water, at a temperature below 20° C., preferably for about 24 hours, to form a compound of formula XIX wherein O=Q— represents —Se(O)φ, and stirring of the reaction mixture at a temperature of 25° to 30° C. for one hour results in decomposition of the compound to a trans-$\Delta^2$-prostaglandin analogue of general formula XI, which can be separated from the reaction medium by methods known per se and, if desired, purified by column chromatography on silica gel.

When the product of formula XVIII is a compound wherein Q is a group —$SR^{12}$, $R^{12}$ being as hereinbefore defined, the product is treated with hydrogen peroxide or sodium periodate in the same way as hereinbefore described for a product of formula XVIII wherein Q is benzeneselenenyl to obtain a compound of general formula XIX wherein Q is a group —$SR^{12}$, $R^{12}$ being as hereinbefore defined, which can be separated from the reaction medium by methods known per se.

When the compound of formula XIX is one wherein Q represents an alkylthio group containing from 1 to 4 carbon atoms, i.e. a group —$SR^{12'}$ (wherein $R^{12'}$ represents an alkyl group containing from 1 to 4 carbon atoms), the compound is dissolved in toluene and the solution stirred, preferably in the presence of a small amount of calcium carbonate, at a temperature of 100° to 120° C. for a period ranging from 5 to 24 hours to decompose the compound to a trans-$\Delta^2$-prostaglandin analogue of general formula XI. When the compound of general formula XIX is one wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a trans-$\Delta^2$-prostaglandin analogue of general formula XI.

The methods hereinbefore described for the preparation of prostaglandin analogues of general formula IX may be represented by the series of reactions depicted schematically below in Scheme A, wherein $R^9$ represents a 2-tetrahydrofuranyl group, a 1-ethoxyethyl group, or a 2-tetrahydropyranyl group unsubstituted or substituted by at least one alkyl group, and the other symbols are as hereinbefore defined.

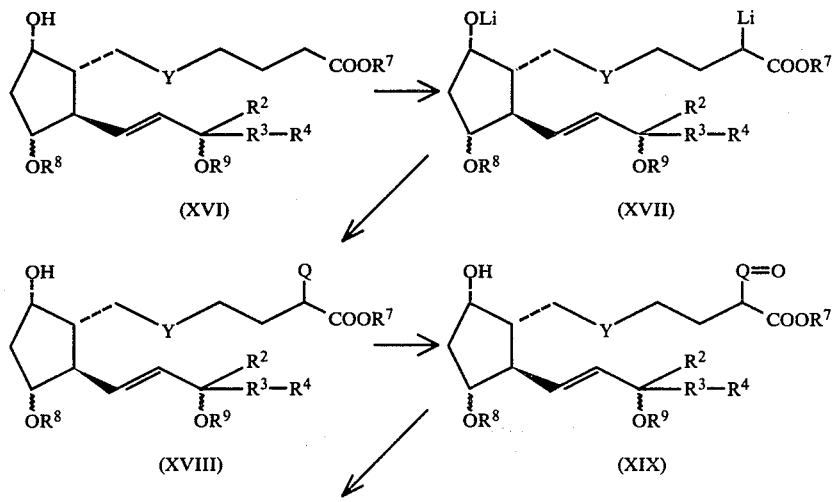

SCHEME A

-continued
SCHEME A

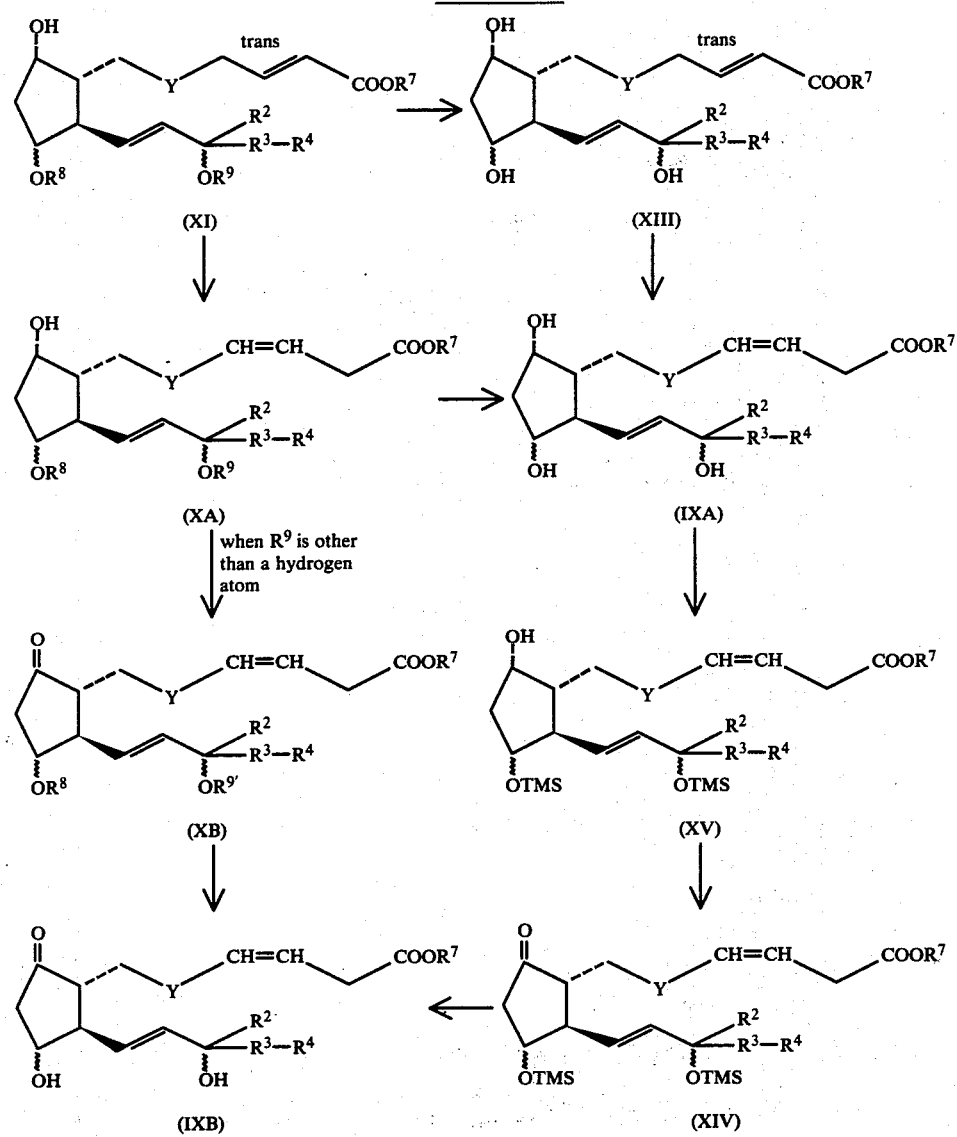

The starting materials of general formula XVI, wherein $R^9$ represents a 2-tetrahydrofuranyl group or a 1-ethoxyethyl group or a 2-tetrahydropyranyl group unsubstituted or substituted by at least one alkyl group and the other symbols are as hereinbefore defined, may be prepared by the sequence of reactions hereinafter depicted schematically in Scheme B:

SCHEME B

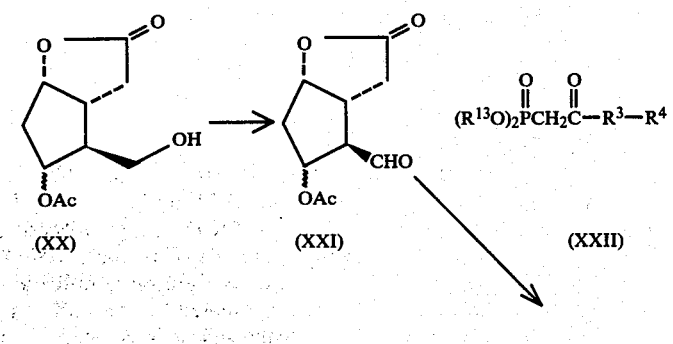

SCHEME B -continued

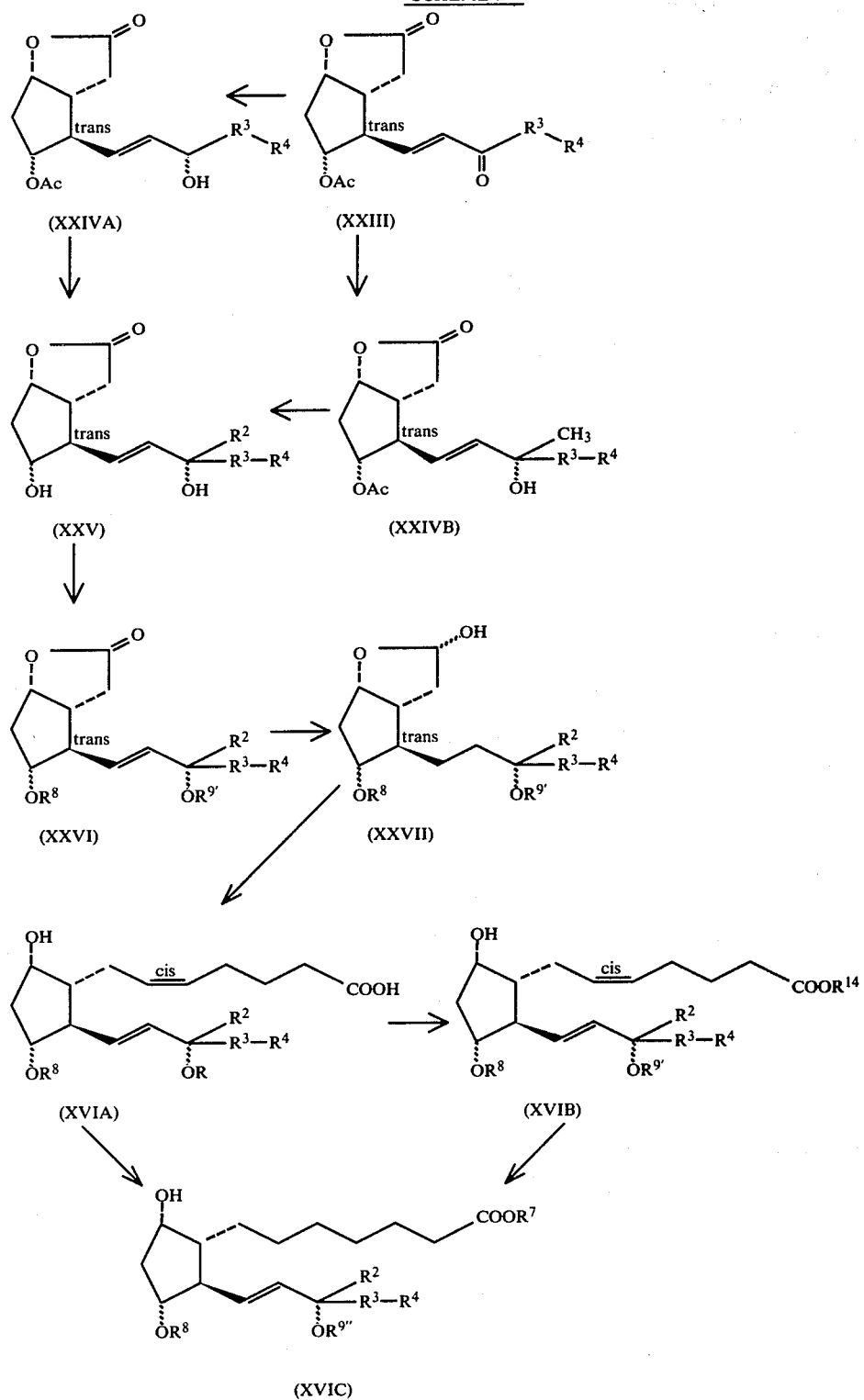

wherein Ac represents the acetyl group, $R^{13}$ represents a straight- or branched-chain alkyl group containing from 1 to 4 carbon atoms, $R^{14}$ represents a straight- or branched-chain alkyl group containing from 1 to 4 carbon atoms, and the other symbols are as hereinbefore defined.

The starting compound of formula XX, wherein the group OAc is in α-configuration, may be prepared as described in J. Amer. Chem. Soc., 91, 5675 (1969) and ibid 92, 397 (1970) by E. J. Corey et al.

A method for the preparation of the bicyclo-octane starting materials of formula XX, wherein the group OAc is in β-configuration, utilizing known procedures may be represented by the series of reactions depicted schematically below in Scheme C [cf. E. J. Corey and Shiro Terashima, Tetrahedron Letters, No. 2, 111-113 (1972)].

SCHEME C

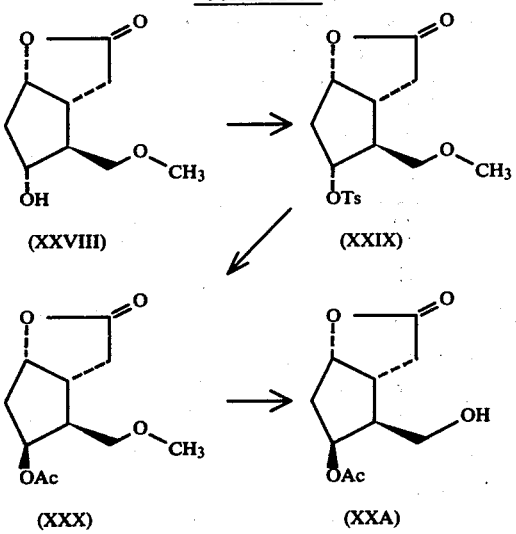

wherein Ts represents the tosyl group and Ac is as hereinbefore defined. The various reactions depicted above in Scheme C may be effected by known methods. A compound of formula XXX may be prepared by reacting a compound of formula XXIX with tetraethylammonium acetate.

A compound of formula XX may be converted to a compound of formula XXI by oxidation under mild conditions, e.g. with Collins' reagent, Jones' reagent, dimethyl- or methylphenylsulphide-N-chlorosuccinimide complex, dimethyl- or methylphenylsulphide-chlorine complex [cf. J. Amer. Chem. Soc., 94, 7586 (1972)], or dicyclohexylcarbodiimide-dimethyl sulphoxide complex [cf. J. Amer. Chem. Soc., 87, 5661 (1965)] at a moderately low temperature.

The reaction of a compound of formula XXI with a dialkyl phosphonate of general formula XXII is preferably effected by suspending sodium hydride in an inert organic solvent, e.g. tetrahydrofuran or 1,2-dimethoxyethane, and adding the dialkyl phosphonate of general formula XXII. The resulting sodio derivative of the dialkyl phosphonate may then be reacted with the compound of general formula XXI at a temperature of 20° C. to 45° C. for one to five hours to form the trans-enone compound of general formula XXIII stereoselectively.

Compounds of general formula XXIVA may be prepared by reducing to a hydroxy group the oxo group in the side chain attached to the bicyclooctane ring of a compound of general formula XXIII. The reduction is suitably effected (1) with excess sodium borohydride in an alkanol containing from 1 to 4 carbon atoms, e.g. methanol, at a low temperature, preferably at −30° C. to −60° C., or (2) with zinc borohydride in a suitable inert organic solvent, e.g. 1,2-dimethoxyethane, at a temperature of −10° C. to 10° C. The product thus obtained is a mixture of isomers in which the hydroxy group is in α- or β-configuration. If desired, the isomer having the hydroxy group in α-configuration may be separated from the isomer having the hydroxy group in β-configuration by column chromatography on silica gel. The separated isomers may be utilised in the procedures herein described to give prostaglandin analogues of general formula VI in which the hydroxy group in position 15 is in α- or β-configuration.

If desired, compounds of general formula XXIII may be converted to compounds of general formula XXIVB by treatment with a Grignard reagent, e.g. methylmagnesium iodide, in an inert organic solvent, e.g. diethyl ether, at a moderately low temperature, e.g. at 0° C., followed by hydrolysis of the resulting organomagnesium compound, for example by treatment with water or an aqueous solution of ammonium chloride or an acid, e.g. hydrochloric acid or oxalic acid, to give a mixture of the α- and β-hydroxy epimers of compounds of general formula XXIVB.

Compounds of general formula XXV may be prepared by hydrolysis under alkaline conditions of compounds of general formula XXIVA and XXIVB, for example by means of anhydrous potassium carbonate in methanol.

Compounds of general formula XXVI may be prepared from compounds of general formula XXV by reaction with a dihydropyran, dihydrofuran or ethyl vinyl ether in an inert organic solvent, e.g methylene chloride, in the presence of a condensing agent, e.g. p-toluenesulphonic acid.

Compounds of general formula XXVII may be prepared by reducing to a hydroxy group the oxo group of compounds of general formula XXVI with diisobutylaluminium hydride in toluene for about 15 minutes at −60° C.

Compounds of general formula XVIA may be prepared from compounds of general formula XXVII by reaction with (4-carboxybutylidene)triphenylphosphorane of formula $(C_6H_5)_3P=CH-(CH_2)_3-COOH$. The reaction between the bicyclooctane of general formula XXVII and (4-carboxybutylidene)triphenylphosphorane [obtained by the reaction of sodium methylsulphinylmethylide with (4-carboxybutyl)triphenylphosphonium bromide]is carried out under the normal conditions utilized for the Wittig reaction, e.g. in an inert organic solvent at ambient temperature. The reaction is preferably carried out in dimethyl sulphoxide because the phosphorane compound is practically insoluble in other solvents, e.g. tetrahydrofuran, and because a cis-double bond must be formed stereospecifically in the Wittig reaction. For the better performance of the wittig reaction more than two molecular equivalents of the phosphorane compound are required for each mole of the bicyclooctane reactant. The reaction is generally effected at a temperature of 10° to 60° C., preferably at 20° to 30° C., and is usually complete after about 30 minutes to four hours at laboratory temperature. The acid product of formula XVIA may be extracted from the reaction mixture by conventional procedures and further purified by column chromatography on silica gel.

If desired, compounds of general formula XVIB may be prepared from compounds of general formula XVIA by esterification, for example by reaction with (i) appropriate diazoalkane compounds, e.g. diazomethane in an inert organic solvent, e.g. diethyl ether, at a temperature of −10° C. to 25° C., preferably at 0° C., (ii) appropriate alcohols in the presence of dicyclohexylcarbodiimide as a condensing agent, (iii) appropriate alcohols following the formation of a mixed acid anhydride by adding a tertiary amine and then a pivaloyl halide or an arylsulphonyl or alkylsulphonyl halide (cf. our British Pat. Nos. 1,362,956 and 1,364,125), (iv) alkyl halides, e.g. methyl iodide, and (a) potassium carbonate in acetone [cf. J. Org. Chem., 34, 3717 (1969)], (b) sodium bicarbonate in N,N-dimethylacetamide or N,N-dimethylformamide [cf. Advan. Org. Chem., 5, 37 (1965)], or (c) calcium oxide in dimethyl sulphoxide [cf. Synthesis, 262 (1972)], or (v) N,N-dimethylformamide-dialkylacetals, e.g. N,N-dimethylformamide-dimethylacetal, in dry benzene [cf. Helv. Chim., Acta, 48,1746 (1965)]. If desired, compounds of general formula XVIA and XVIB may be reduced to give compounds of general formula XVIC. Suitably the reduction may be effected by hydrogenation in the presence of a hydrogenation catalyst, e.g palladium on carbon or palladium black, in an inert organic solvent, for example a lower alkanol, e.g. methanol or ethanol, at laboratory temperature at normal or elevated pressure, e.g. at a hydrogen pressure from atmospheric to 15 kg/cm².

The dialkyl phosphonates of general formula XXII may be prepared by reacting a solution of n-butyllithium in an inert organic solvent, e.g. n-hexane, n-pentane or diethyl ether, with a solution of a dialkyl methylphosphonate of the general formula:

(XXXI)

(wherein $R^{13}$ is as hereinbefore defined), e.g. dimethyl methylphosphonate or diethyl methylphosphonate, at a temperature below $-50°$ C., and then adding dropwise to the reaction mixture a solution of a compound of the general formula:

(XXXII)

(wherein $R^3$ and $R^4$ are as hereinbefore defined and $R^{15}$ represents a lower alkyl group, preferably containing from 1 to 4 carbon atoms, e.g. methyl or ethyl) in tetrahydrofuran at a temperature below $-50°$ C., stirring the reaction mixture below $-50°$ C., for 1.5 hours and then stirring for 18 hours at 0° C. to give the desired dialkyl phosphonate of general formula XXII.

Compounds of general formula XVI, wherein $R^9$ represents a hydrogen atom and the other symbols are as hereinbefore defined, may be prepared by the hydrolysis under alkaline conditions of compounds of the general formula:

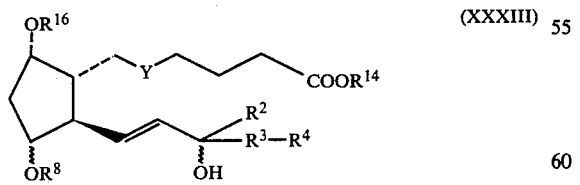

(XXXIII)

wherein $R^{16}$ represents an alkylcarbonyl group containing from 2 to 5 carbon atoms and the other symbols are as hereinbefore defined. The hydrolysis under alkaline conditions may be effected with (1) an aqueous solution of an alkali metal, e.g. sodium or potassium, hydroxide or carbonate in the presence of a water miscible solvent, e.g. tetrahydrofuran or an alkanol containing from 1 to 4 carbon atoms, to give compounds of general formula XVI wherein $R^7$ represents a hydrogen atom, or (2) with anhydrous potassium carbonate in an anhydrous alkanol containing from 1 to 4 carbon atoms, preferably absolute methanol, to give compounds of general formula XVI wherein $R^7$ represents an alkyl group containing from 1 to 4 carbon atoms.

Compounds of general formula XXXIII may be prepared from compounds of the general formula:

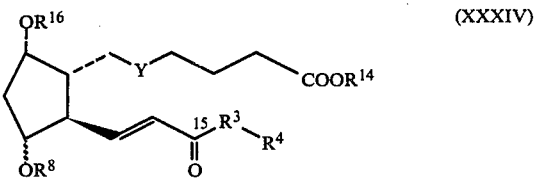

(XXXIV)

(wherein the various symbols are as hereinbefore defined) by converting the 15-oxo group to a hydroxy group by methods known per se. The conversion may be carried out by means heretofore mentioned for the conversion of compounds of general formula XXIII to those of general formulae XXIVA and XXIVB. The product of general formula XXXIII thus obtained is a mixture of isomers in which the hydroxy group at position 15 is in $\alpha$- or $\beta$-configuration. If desired, the isomer having the hydroxy group in $\alpha$- configuration may be separated from the isomer having the hydroxy group in $\beta$-configuration by column chromatography on silica gel. The separated isomers may be utilized in the procedures herein described to give prostaglandin analogues of general formula VI in which the hydroxy group in position 15 is in $\alpha$- or $\beta$-configuration.

Compounds of general formula XXXIV, wherein the various symbols are as hereinbefore defined, may be prepared by the Wittig reaction of a compound of the general formula:

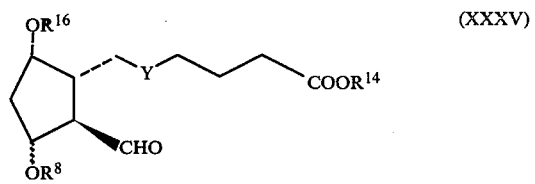

(XXXV)

(wherein the various symbols are as hereinbefore defined) with the sodio derivative of a dialkyl phosphonate of general formula XXII, wherein the various symbols are as hereinbefore defined, preferably using the same reaction conditions as are mentioned heretofore for the reaction of compounds of general formula XXI with those of general formula XXII.

Compounds of general formula XXXV, wherein the various symbols are as hereinbefore defined, used as starting materials in the hereinbefore described procedure, may themselves be prepared by methods known per se from compounds of general formula XXXVI by the series of reactions depicted schematically below in Scheme D:

SCHEME D

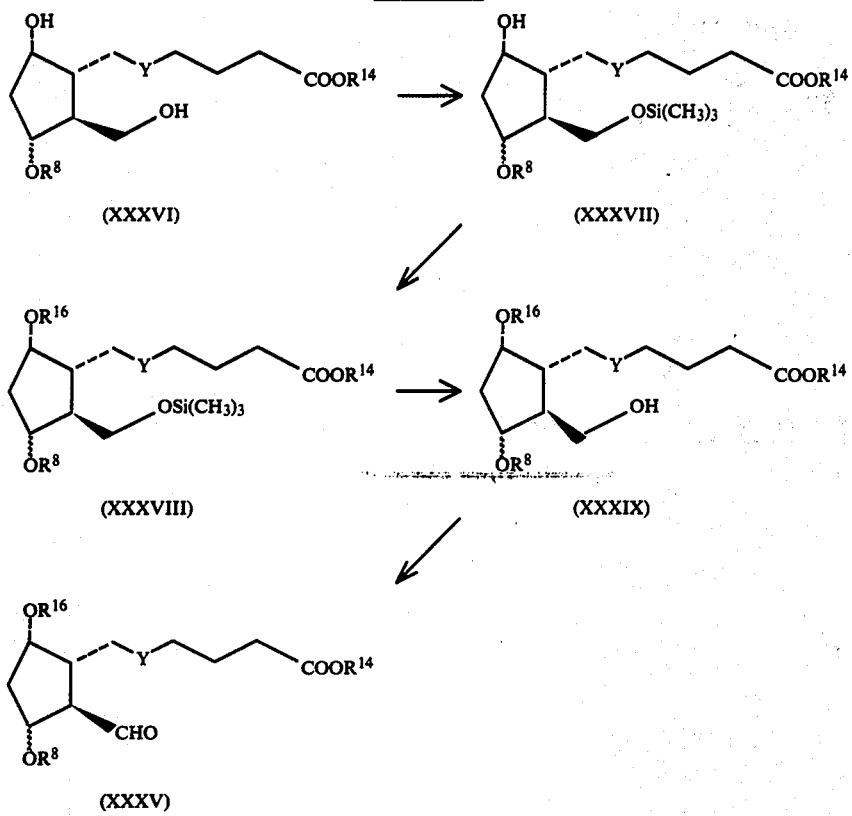

wherein Y, $R^8$, $R^{14}$ and $R^{16}$ are as hereinbefore defined and preferably $R^{16}$ represents an acetyl group.

Compounds of general formula XXXVII may be prepared by reacting compounds of general formula XXXVI with trimethylchlorosilane in an inert organic solvent, e.g. methylene chloride, in the presence of a base, e.g. pyridine or a tertiary amine, at a low temperature, e.g. at a temperature of −30° C. to 0° C. Compounds of general formula XXXVIII may be prepared by reacting a trimethylsilyl ether of general formula XXXVII with an appropriate acyl chloride or acid anhydride in an inert organic solvent, e.g. methylene chloride, in the presence of a base, e.g. pyridine or a tertiary amine, at a low temperature, e.g. at a temperature of 0° C. to 30° C. Compounds of general formula XXXIX may be prepared by treating compounds of general formula XXXVIII by methods known per se for the removal of the trimethylsilyl group, for example by treatment with an acid: it is preferable not to use a strong acid in order to avoid the risk of the removal of the group $R^8$. Compounds of general formula XXXIX may be converted to compounds of general formula XXXV under mild and neutral conditions, e.g. with chromium trioxide-pyridine complex or Jones' reagent at a moderately low temperature.

Compounds of general formula XXXVI may be prepared by the methods described in Japanese Patent Publication No. 49-102646 from compounds of formula XX which may be represented by the series of reactions depicted schematically below in Scheme E, wherein the various symbols are as hereinbefore defined.

SCHEME E

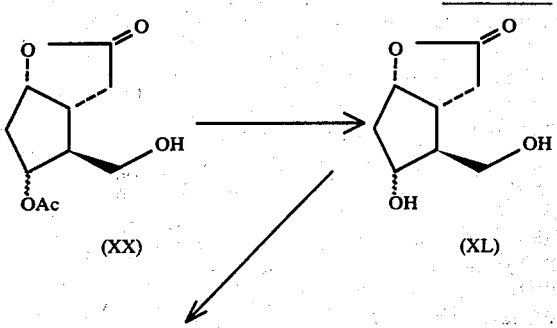

-continued
SCHEME E

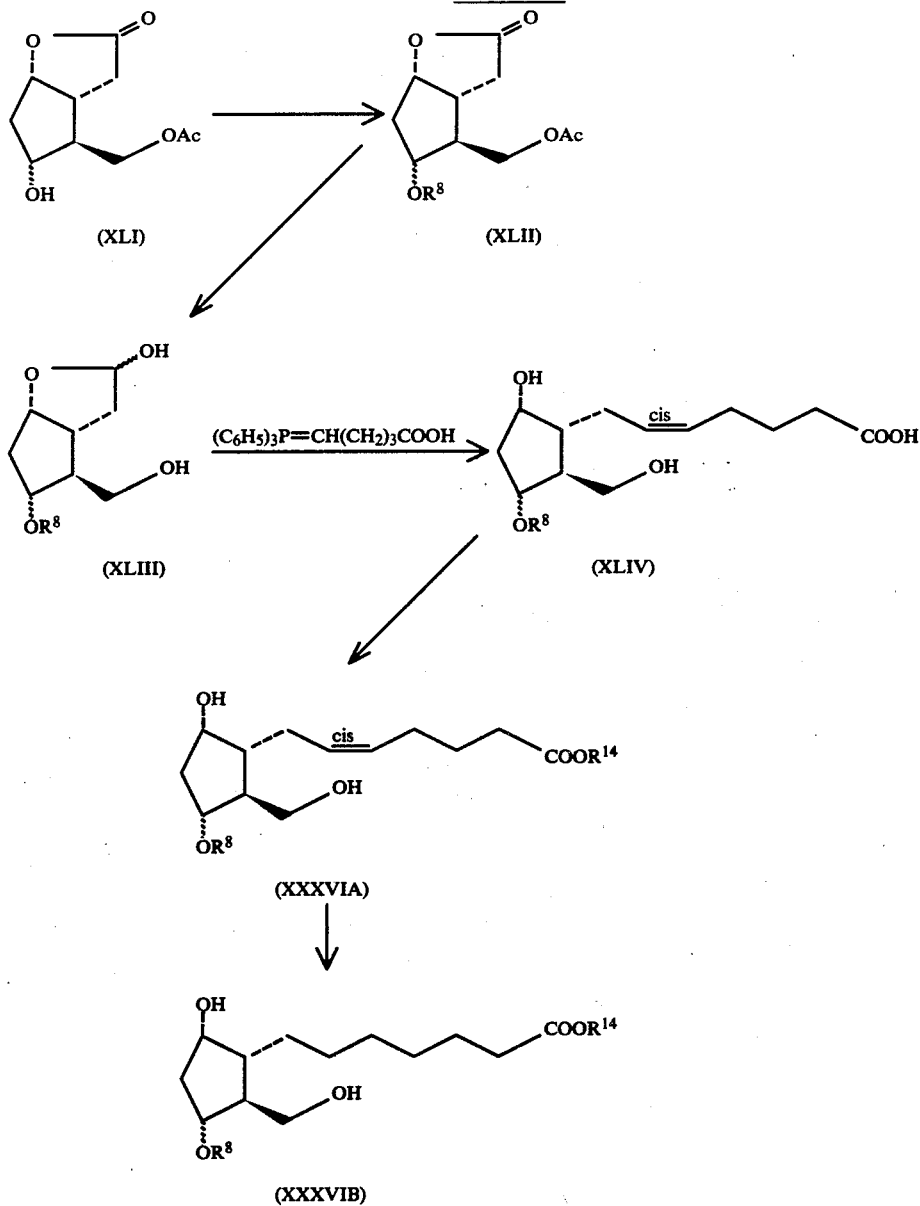

Compounds of general formula XL may be prepared by hydrolysis under alkaline conditions of compounds of formula XX, for example using potassium hydroxide in methanol. Compounds of formula XLI may be obtained by the acetylation of compounds of formula XL under mild conditions and may be converted to compounds of general formula XLII by reaction with a dihydropyran, dihydrofuran or ethyl vinyl ether in an inert organic solvent, e.g. methylene chloride, in the presence of a condensing agent, e.g. p-toluenesulphonic acid. Compounds of general formula XLIII may be prepared by reducing compounds of general formula XLII with diisobutylaluminium hydride in toluene for about 15 minutes at −60° C. Dimsyl anion, previously prepared from sodium hydride and dimethyl sulphoxide, is reacted with (4-carboxybutyl)triphenylphosphonium bromide to form (4-carboxybutyldiene)triphenylphosphorane. To that compound is added a compound of general formula XLIII and the mixture in dimethyl sulphoxide is made to react for 2 hours at room temperature to yield compounds of general formula XLIV. The acids of general formula XLIV are then esterified to compounds of general formula XXXVIA using a method heretofore mentioned for the esterification of compounds of general formula XVIA to those of general formula formula XVIB. If desired, compounds of general formula XXXVIA may be reduced to give compounds of general formula XXXVIB by means heretofore mentioned for the reduction of compounds of general formulae XVIA and XVIB to those of general formula XVIC.

If desired, compounds of general formula XIII, wherein the various symbols are as hereinbefore defined, may be prepared by the series of reactions depicted in Scheme A (XVI→XVII→XVIII→XIX→XI→XIII) but replacing the compounds of general formula XVI by compounds of the general formula:

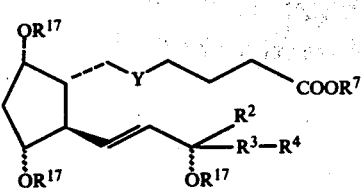

(XLV)

wherein $R^{17}$ represents a 2-tetrahydrofuranyl group or a 1-ethoxyethyl group or a 2-tetrahydropyranyl group unsubstituted or substituted by at least one alkyl group and the other symbols are as hereinbefore defined.

Compounds of general formula XLV may be prepared from compounds of general formula XVI by reaction with a dihydropyran, dihydrofuran or ethyl vinyl ether in an inert organic solvent, e.g. methylene chloride, in the presence of a condensing agent, e.g. p-toluenesulphonic acid.

Compounds of general formula XXXIII, wherein $R^4$ is other than a grouping of formula VIII, and the other symbols are as hereinbefore defined, may also be prepared from compounds of general formula XXXV by the series of reactions depicted schematically below in Scheme F, wherein $R^3$ is as hereinbefore defined and $R^{4'}$ represents a cycloalkyl group containing from 5 to 7 carbon atoms or a grouping of formula VII, or $R^3$ and $R^{4'}$ together represent a straight- or branched-chain alkyl group containing from 1 to 10 carbon atoms, and the other symbols are as hereinbefore defined.

Compounds of general formula XXXIII, wherein $R^2$ represents a hydrogen atom and the other symbols are as hereinbefore defined [hereinbefore depicted in formula XXXIIIA], may be prepared from compounds of general formula XLVI by the Grignard reaction with a Grignard reagent of the general formula HalMg-$R^3$—$R^{4'}$ (wherein Hal represents a halogen atom and the other symbols are as hereinbefore defined) in an inert organic solvent, e.g. diethyl ether, at a low temperature, e.g. at 0° C., followed by hydrolysis of the resulting organomagnesium compounds, for example by treatment with water or an aqueous solution of ammonium chloride or an acid, e.g. hydrochloric acid or oxalic acid, to give a mixture of the 15α- and 15β-hydroxy epimers of compounds of general formula XXXIIIA. It is sometimes possible to separate the 15α-hydroxy epimer from the 15β-hydroxy epimer by column chromatography on silica gel.

If desired, compounds of general formula XXXIII wherein $R^2$ represents a methyl group and the other symbols are as hereinbefore defined, i.e. compounds of general formula XXXIIIB, may be prepared from compounds of general formula XXXIIIA by oxidation with a chromic acid solution (e.g. obtained from chromium trioxide, manganese sulphate and sulphuric acid in water) or Jones' reagent, and then by the Grignard reaction of the resulting compound of general formula XXXIV with a methylmagnesium halide followed by hydrolysis of the organomagnesium compound so formed.

SCHEME F

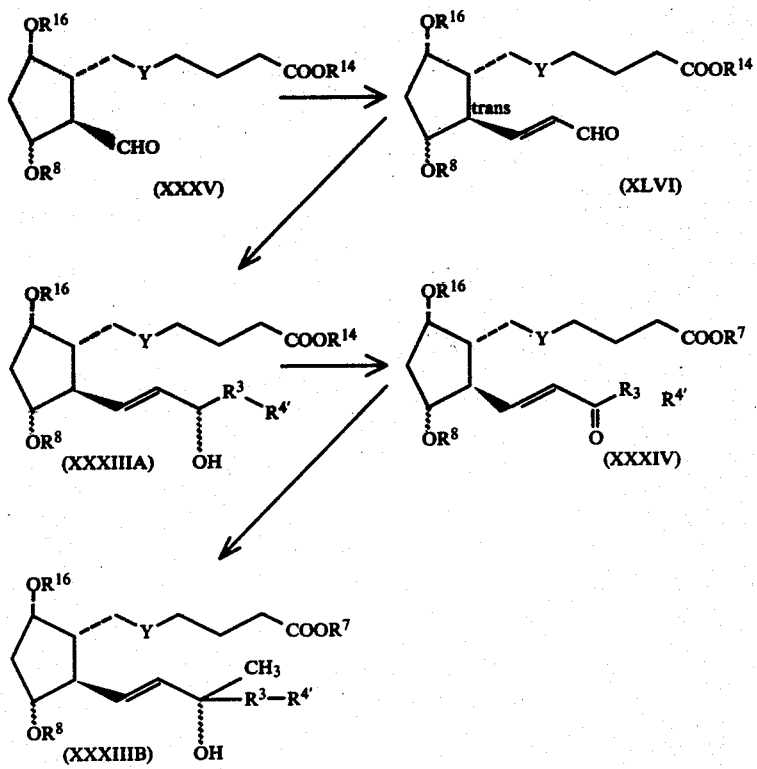

Compounds of general formula XLVI, wherein the various symbols are as hereinbefore defined, may be prepared from compounds of general formula XXXV by reaction with formylmethylenetriphenylphosphorane in an inert organic solvent, e.g. benzene, at about 70° C. for several hours, e.g. 20 hours.

Compounds of general formula XVI, wherein $R^9$ represents a 2-tetrahydrofuranyl group or a 1-ethoxyethyl group or a 2-tetrahydropyranyl group unsubstituted or substituted by at least one alkyl group and the other symbols are as hereinbefore defined, may also be prepared from compounds of general formula XXXIII by the sequence of reactions hereinafter depicted schematically in Scheme G, wherein the various symbols are as hereinbefore defined.

sion of compounds of general formula XXXIII to those of general formula XVI.

Compounds of general formula XLVI, wherein Y represents cis-vinylene and the other symbols are as hereinbefore defined, may also be prepared by the sequences of reactions hereinafter depicted schematically in Scheme H, wherein $R^{18}$ represents a straight- or branched-chain alkyl group containing from 1 to 4 carbon atoms and the other symbols are as hereinbefore defined.

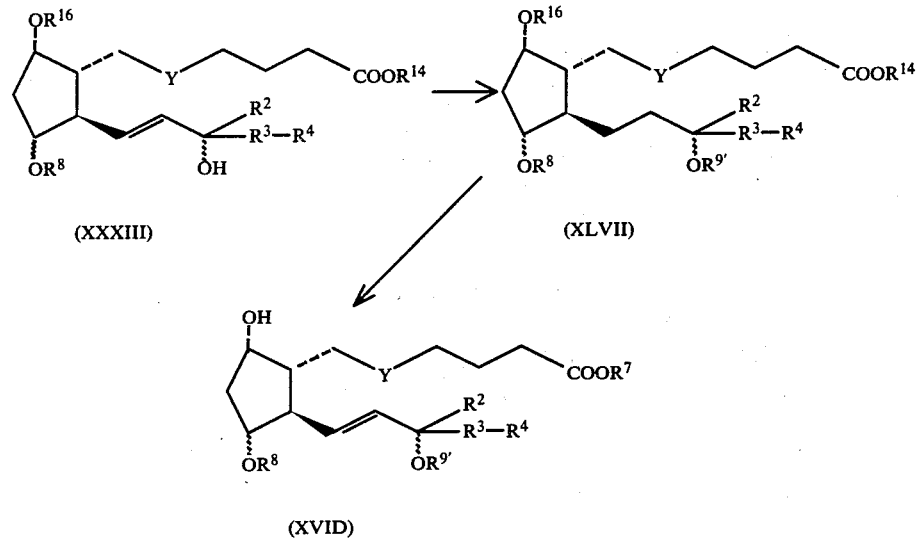

The conversion of compounds of general formula XXXIII to those of general formula XLVII may be carried out by means heretofore mentioned for the conversion of compounds of general formula XXV to those of general formula XXVI.

The conversion of compounds of general formula XLVII to those of general formula XVID may be carried out by means heretofore mentioned for the conversion of compounds of general formula XXXIII to those of general formula XVI.

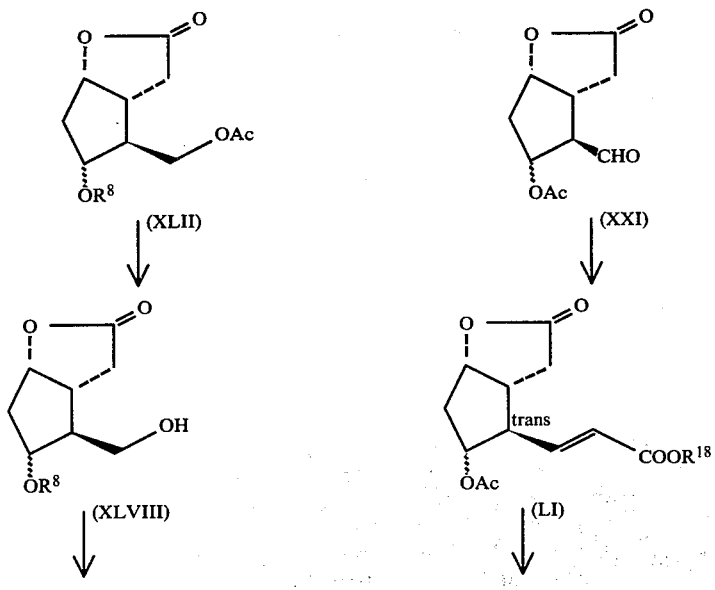

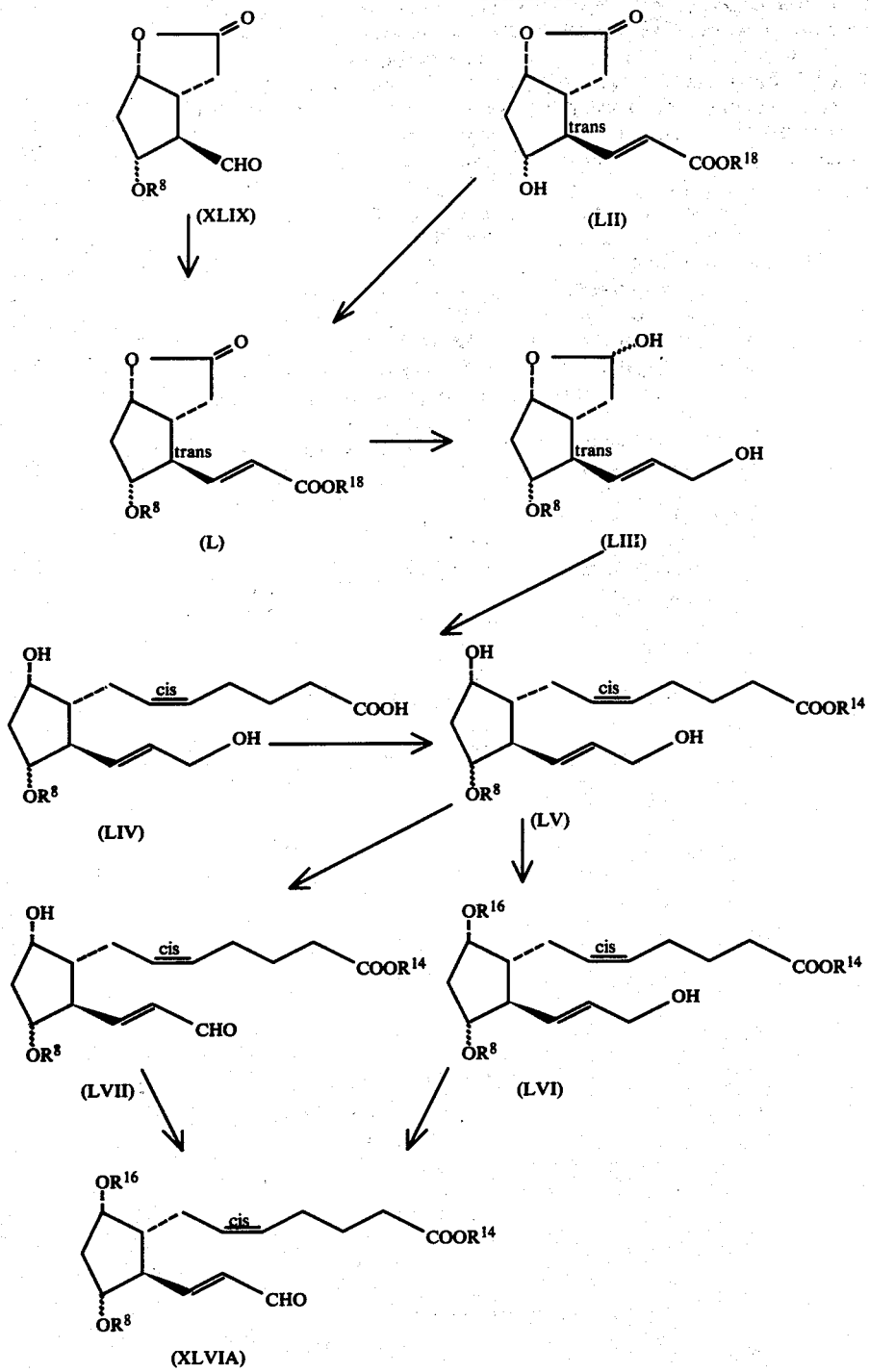

Referring to Scheme H, compounds of general formula XLII may be converted to compounds of general formula XLVIII by deacetylation with anhydrous potassium carbonate in absolute methanol.

Compounds of general formula XLVIII may be converted to compounds of general formula XLIX by oxidation under mild conditions, e.g. with Collins' reagent at a moderately low temperature.

Compounds of general formula XLIX may be transformed stereospecifically to trans-α,β-unsaturated esters of general formula L by reaction with the sodio derivatives of the general formula:

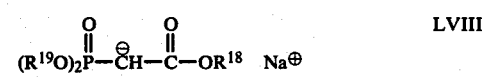

(wherein $R^{18}$ is as hereinbefore defined and $R^{19}$ represents an alkyl group containing from 1 to 4 carbon atoms) in an inert organic solvent, e.g. tetrahydrofuran or 1,2-dimethoxyethane, at a temperature of 0° to 30° C. for 2 hours, in a high yield, e.g. 70% to 90%.

Compounds of general formula L may also be prepared from compounds of general formula XXI via formula LI and formula LII. The conversion of compounds of formula XXI to those of general LI may be carried out by means heretofore mentioned for the conversion of compounds of general formula XLIX to those of general formula L. Compounds of general formula LI may be converted to compounds of general formula L by selective deacetylation with an equimolar amount of anhydrous potassium carbonate in absolute methanol and then etherification with a dihydropyran, or dihydrofuran or ethyl vinyl ether in an inert organic solvent, e.g. methylene chloride, in the presence of a condensing agent, e.g. p-toluenesulphonic acid.

Compounds of general formula L may be converted quantitatively to compounds of general formula LIII by reduction with more than three molar equivalents of diisobutylaluminium hydride in an inert organic solvent, e.g. toluene, n-pentane or n-hexane, at a low temperature, e.g. $-78°$ C. to $-20°$ C.

The conversion of compounds of general formula LIII to those of general formula LIV may be carried out by means heretofore mentioned for the conversion of compounds of general formula XXVII to those of general formula XVIA.

The esterification of compounds of general formula LIV to those of general formula LV may be carried out by means heretofore mentioned for the reaction of compounds of general formula XVIA to those of general formula XVIB.

Compounds of general formula LV may be converted to compounds of general formula LVI by reaction with trimethylchlorosilane in an inert organic solvent, e.g. methylene chloride, in the presence of a base, e.g. pyridine or a tertiary amine, at a low temperature, e.g. at a temperature of $-30°$ to $0°$ C., then reacting the resulting trimethylsilyl ether with an appropriate acyl halide or acid anhydride in an inert organic solvent, e.g. methylene chloride, in the presence of a base, e.g. pyridine or a tertiary amine, at a low temperature, e.g. at a temperature of $0°$ to $30°$ C., and treating the resulting acyl ether by methods known per se for the removal of the trimethylsilyl group, for example by treatment with an acid; it is preferable not to use a strong acid in order to avoid the risk of the removal of the group $R^8$.

Compounds of general formula LVI may be converted to compounds of general formula XLVIA by oxidation with manganese dioxide, for example in an inert organic solvent, e.g. methylene chloride, at laboratory temperature, which oxidizes an allylic alcohol group selectively.

Compounds of general formula XLVIA may be prepared from compounds of general formula LV by oxidation with manganese dioxide in an inert organic solvent, e.g. methylene chloride, at laboratory temperature, and then acylation of the resulting compound of general formula LVII.

According to a further feature of the present invention, compounds of general formula IXA are prepared from compounds of general formula XXXVI by the series of reactions depicted schematically below in Scheme I, wherein $R^{20}$ represents the benzoyl or acetyl group, and the other symbols are as hereinbefore defined.

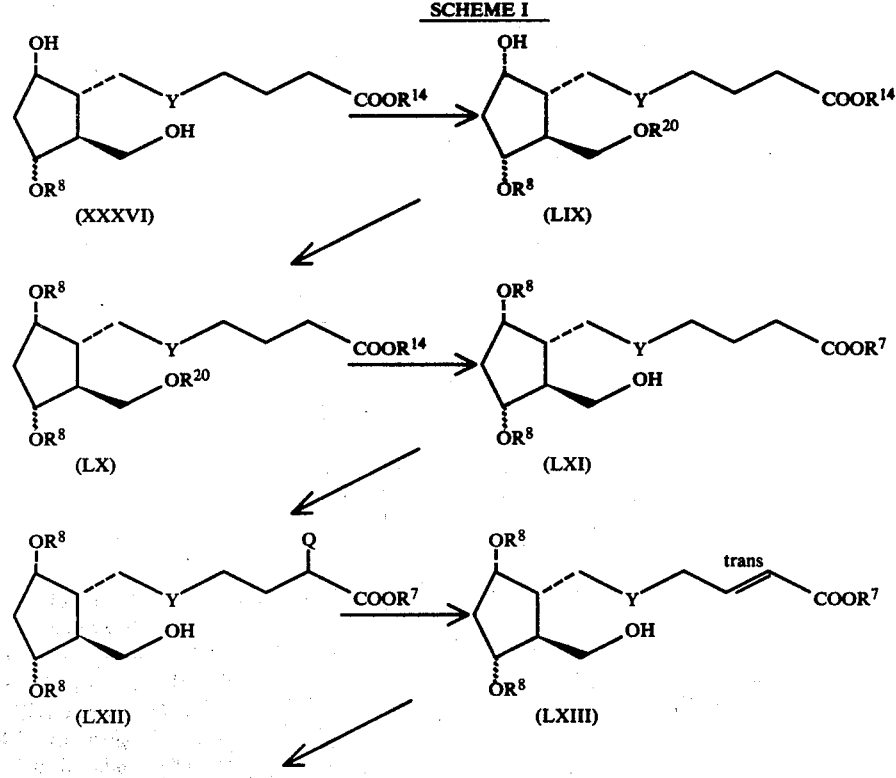

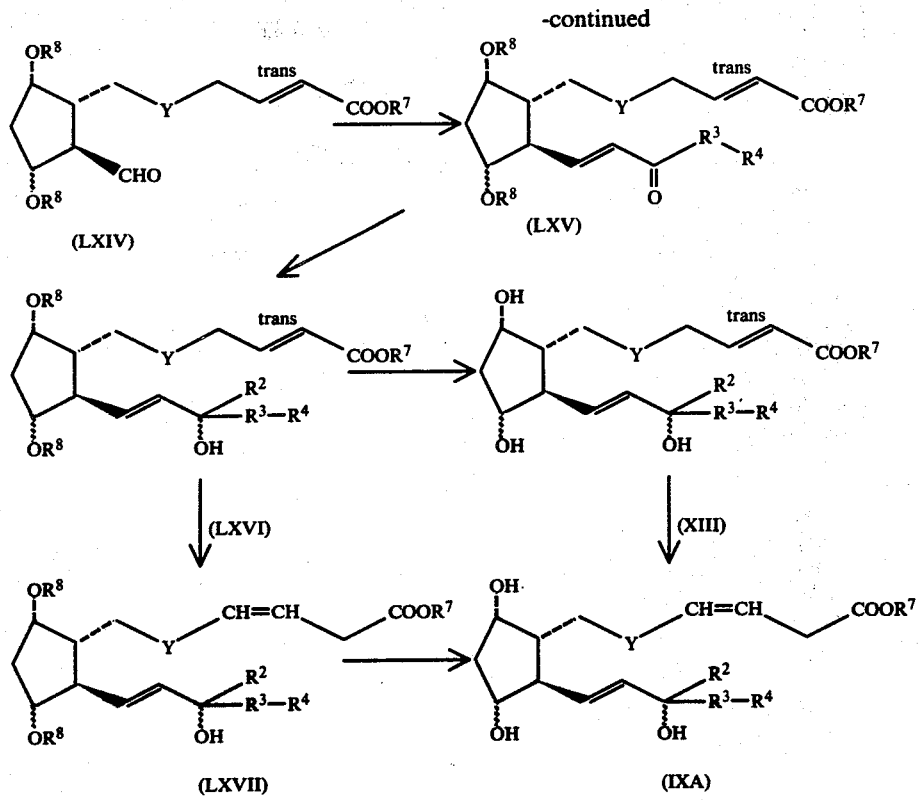

Compounds of general formula LIX may be prepared from compounds of general formula XXXVI by reaction (1) with benzoyl chloride in an inert organic solvent, e.g. methylene chloride, in the presence of a base, e.g. pyridine or a tertiary amine, at a moderately low temperature, preferably at −20° to −25° C., or (2) with acetyl chloride or acetic anhydride in an inert organic solvent, e.g. methylene chloride, in the presence of a base, e.g. pyridine or a tertiary amine, at a low temperature of 0° to 30° C., and may be converted to compounds of general formula LX by means heretofore mentioned for the conversion of compounds of general formula XXV to those of general formula XXVI.

Compounds of general formula LXI may be prepared from compounds of general formula LX by means heretofore mentioned for the conversion of compounds of general formula XXXIII to those of general formula XVI.

The series of reactions LXI→LXIII (via LXII) may be effected as hereinbefore described for the series of reactions XVI→XI (via XVII, XVIII and XIX) in Scheme A.

The series of reactions LXIII→LXVI (via LXIV and LXV) may be effected as hereinbefore described for the series of reactions XX→XXIVA or XXIVB (via XXI and XXIII) in Scheme B.

Compounds of general formula LXVII may be prepared from compounds of general formula LXVI by means heretofore mentioned for the conversion of compounds of general formula XI to those of general formula XA, and may be converted to compounds of general formula IXA by means heretofore mentioned for the conversion of compounds of general formula X to those of general formula IX.

Compounds of general formula IXA may also be prepared from compounds of general formula LXVI via compounds of general formula XIII.

The conversion of compounds of general formula LXVI to those of general formula XIII may be carried out by means heretofore mentioned for the conversion of compounds of general formula X to those of general formula IX.

According to a further feature of the present invention, compounds of general formula IXA are also prepared from compounds of general formula XIII by the series of reactions depicted schematically below in Scheme J, wherein the various symbols are as hereinbefore defined.

SCHEME J

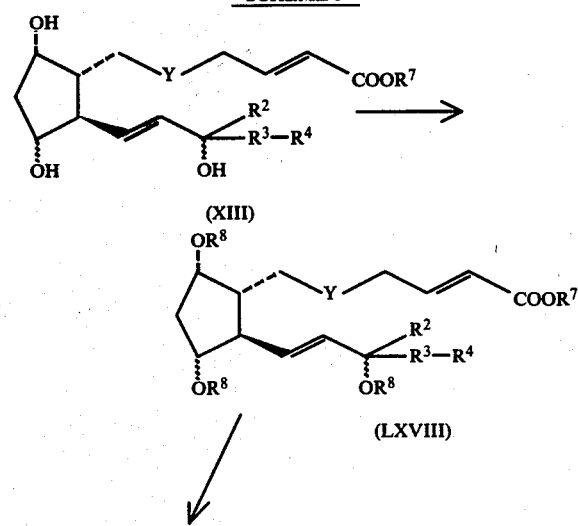

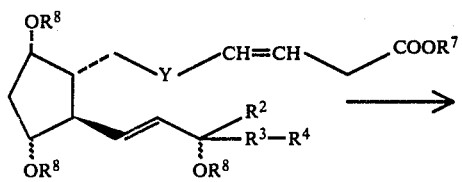

(LXIX)

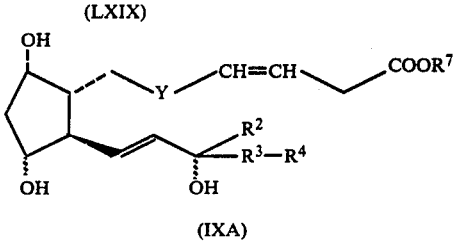

(IXA)

The conversion of compounds of general formula XIII to those of general formula LXVIII may be carried out by means heretofore mentioned for the conversion of compounds of general formula XXV to those of general formula XXVI.

The series of reactions LXVIII→IXA (via LXIX) may be effected as hereinbefore described for the series of reactions XI→IXA (via XA) in Scheme A.

According to a further feature of the present invention, compounds of general formula VI, wherein X represents ethylene or trans-vinylene, R¹ represents a hydrogen atom or a straight- or branched-chain alkyl group containing from 1 to 4 carbon atoms, the double bonds between C₃-C₄ and C₁₃-C₁₄ are trans, and the other symbols are as hereinbefore defined, i.e. compounds of the general formula:

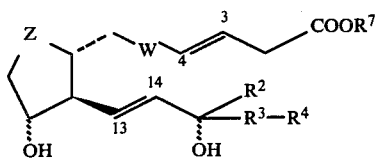

LXX (wherein W represents ethylene or trans-vinylene, and the other symbols are as hereinbefore defined) are prepared from compounds of general formula IXA, wherein the various symbols are as hereinbefore defined, by the series of reactions depicted schematically below in Scheme K, wherein the various symbols are as hereinbefore defined.

SCHEME K

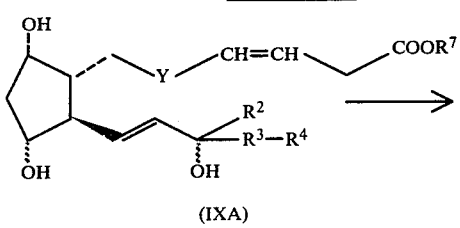

(IXA)

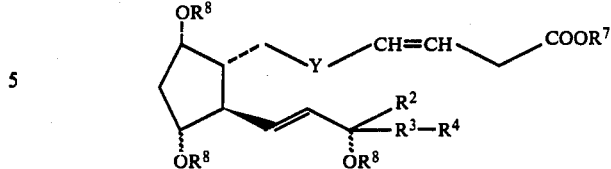

(LXIX)

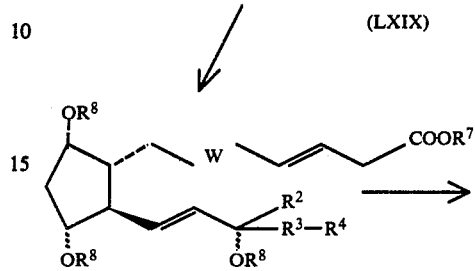

(LXXI)

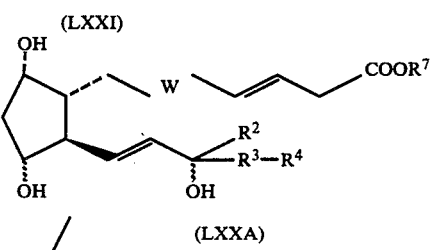

(LXXA)

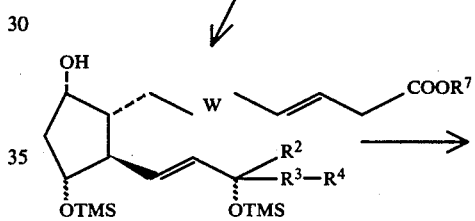

(LXXII)

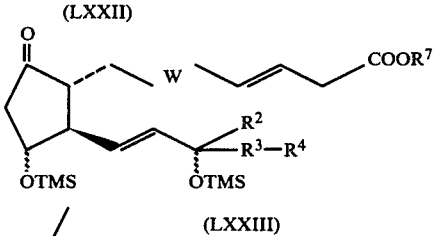

(LXXIII)

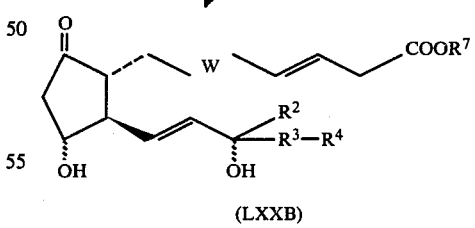

(LXXB)

The conversion of compounds of general formula IXA to those of general formula LXIX may be carried out by means heretofore mentioned for the conversion of compounds of general formula XXV to those of general formula XXVI.

The photoisomerization of compounds of general formula LXIX to those of general formula LXXI may be carried out by irradiation (i) when Y represents cis-vinylene, with diffuse laboratory light in carbon tetrachloride in the presence of iodine at room temperature

[cf. J. Amer. Chem. Soc. 75, 3430 (1953)], or (ii) when Y represents ethylene, with light from a high pressure mercury lamp in an inert organic solvent, e.g. benzenemethanol mixture, in the presence of diphenyl sulphide or diphenyl disulphide at room temperature.

The conversion of compounds of general formula LXXI to those of general formula LXXA may be carried out by means heretofore mentioned for the conversion of compounds of general formula X to those of general formula IX.

The series of reactions LXXA→LXXB (via LXXII and LXXIII) may be effected as hereinbefore described for the series of reactions IXA→IXB (via XV and XIV) in Scheme A.

The present invention accordingly provides a process for the preparation of prostaglandin analogues of general formula VI wherein Z represents

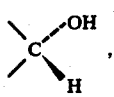

$R^1$ represents a hydrogen atom or a straight- or branched-chain alkyl group containing from 1 to 4 carbon atoms, and the other symbols are as hereinbefore defined, i.e. compounds of the general formula:

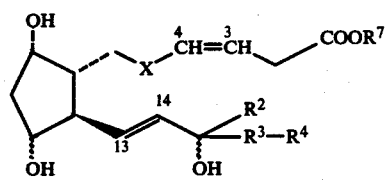
VIA (wherein the various symbols are as hereinbefore defined and (1) the double bond between $C_3$-$C_4$ is trans or cis, or trans and cis, when X is cis-vinylene or ethylene and (2) the double bond between $C_3$-$C_4$ is trans, when X is trans-vinylene and the double bond between $C_{13}$-$C_{14}$ is trans) which comprises hydrolysing a compound of the general formula:

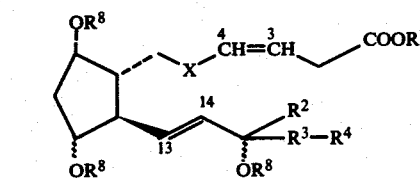
LXIXA wherein the various symbols are as hereinbefore defined, the double bond between $C_3$-$C_4$ is as hereinbefore specified in relation to compounds of general formula VIA and the double bond between $C_{13}$-$C_{14}$ is trans.

The conversion of compounds of general formula LXIXA to those of formula VIA may be effected as hereinbefore described for the conversion of compounds of general formula XA to those of general formula IXA.

It is to be understood that in formulae VIB and XIVA below the double bond depicted in the grouping

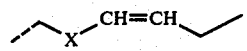

attached to the cyclopentane ring is as specified above in relation to compounds of general formula VIA, and the double bond between $C_{13}$-$C_{14}$ is trans.

The invention accordingly also provides a process for the preparation of prostaglandin analogues of general formula VI wherein $R^1$ represents a hydrogen atom or a straight- or branched-chain alkyl group containing from 1 to 4 carbon atoms and Z represents

i.e. compounds of the general formula:

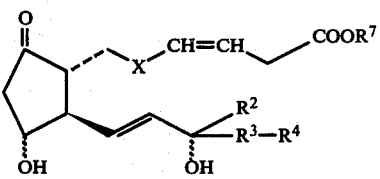
VIB (wherein the various symbols are as hereinbefore defined) which comprises hydrolysing the silyloxy groups of a compound of the general formula:

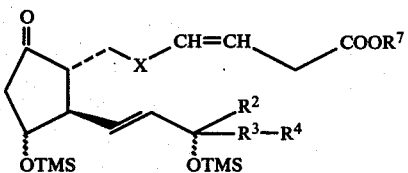
XIVA (wherein the various symbols are as hereinbefore defined) to hydroxy groups under extremely mild acidic conditions.

The conversion of compounds of general formula XIVA to those of formula VIB may be effected as hereinbefore described for the conversion of compounds of general formula XIV to those of general formula IXB.

According to a further feature of the present invention, the compounds of general formula VI, wherein $R^1$ represents a straight- or branched-chain alkyl group containing from 1 to 12 carbon atoms and the other symbols are as hereinbefore defined, are prepared by esterification of the corresponding acids of general formula VI, wherein $R^1$ represents a hydrogen atom and the other symbols are as hereinbefore defined, by methods known per se, for example by reaction with (i) appropriate diazoalkanes in an inert organic solvent, e.g. diethyl ether, at a temperature of $-10°$ to 25° C., preferably at 0° C., (ii) appropriate alcohols in the presence of dicyclohexylcarbodiimide as a condensing agent, or (iii) appropriate alcohols following formation of a mixed anhydride by adding a tertiary amine and pivaloyl halide or an alkylsulphonyl halide or arylsulphonyl halide (cf. our British Patent Nos. 1,362,956 and 1,364,125).

Compounds of general formula VI, wherein $R^1$ represents a hydrogen atom and the other symbols are as hereinbefore defined, may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VI are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula VI wherein $R^1$ represents a hydrogen atom by, for example, reaction of stoichiometric quantities of an acid of general formula VI and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula VI may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the prostaglandin analogues.

The prostaglandin analogues of general formula VI and their cyclodextrin clathrates and, when $R^1$ in formula VI represents a hydrogen atom, their non-toxic salts possess the valuable pharmacological properties typical of the prostaglandins in a selective fashion, in particular stimulatory activity on uterine contraction and abortifacient, luteolytic and antinidatory activity, and are useful in the termination of pregnancy and induction of labour in pregnant female mammals and in the treatment of impaired fertility, in the control of oestrus, contraception and menstrual regulation in female mammals. For example, in standard laboratory tests, (i) 17-phenyl-18,19,20-trinor-trans and cis-$\Delta^3$-PGF$_{2\alpha}$ methyl ester, 16-(3-trifluoromethylphenoxy)-17,18,19,20-tetranor-trans and cis-$\Delta^3$-PGF$_{2\alpha}$ methyl ester, 16-(3-chlorophenoxy)-17,18,19,20-tetranor-trans and cis-$\Delta^3$-PGF$_{2\alpha}$ methyl ester, 16-phenoxy-17,18,19,20-tetranor-trans and cis-$\Delta^3$-PGF$_{2\alpha}$ methyl ester, 16-(3-chlorophenoxy)-17,18,19,20-tetranor-cis-$\Delta^3$-PGF$_{2\alpha}$ methyl ester, 16-(3-chlorophenoxy)-17,18,19,20-tetranor-trans-$\Delta^3$-PGF$_{2\alpha}$ methyl ester, 16-phenoxy-17,18,19,20-tetranor-cis-$\Delta^3$-PGF$_{2\alpha}$ methyl ester, 16-phenoxy-17,18,19,20-tetranor-trans-$\Delta^3$-PGF$_{2\alpha}$ methyl ester, 16-(4-chlorophenoxy)-17,18,19,20-tetranor-trans and cis-$\Delta^3$-PGF$_{2\alpha}$ methyl ester, methyl 9$\alpha$,1-1$\alpha$,15$\alpha$-trihydroxy-16-phenoxy-17,18,19,20-tetranor-prosta-trans-3,trans-5,trans-13-trienoate, methyl 9$\alpha$,1-1$\alpha$,15$\alpha$-trihydroxy-16-(3-chlorophenoxy)-17,18,19,20-tetranorprosta-trans-3,trans-5,trans-13-trienoate and 16-phenoxy-17,18,19,20-tetranor-trans and cis-$\Delta^3$-PGF$_{1\alpha}$ methyl ester inhibit implantation in the pregnant female rat when administered subcutaneously on the 3rd, 4th and 5th days of pregnancy at the daily doses of 200, 50, 5, 5, 10, 5, 10, 5, 10, 20, 20 and 100 $\mu$g/kg animal body weight, respectively; (ii) 16-(3-trifluoromethylphenoxy)-17,18,19,20-tetranor-trans and cis-$\Delta^3$-PGF$_{2\alpha}$ methyl ester, 16-(3-chlorophenoxy)-17,18,19,20-tetranor-trans and cis-$\Delta^3$-PGF$_{2\alpha}$ methyl ester and 16-phenoxy-17,18,19,20-tetranor-trans and cis-$\Delta^3$-PGF$_{2\alpha}$ methyl ester produce an abortifacient effect in the pregnant female rat when administered intraperitoneally on the 17th day of pregnancy at the daily doses of 10.0, 2.0 and 1.0 $\mu$g/kg animal body weight, respectively; (iii) in tests for luteolytic effect [Rats are hysterectomized on the 5th day of gestation (day 0=sperm confirmation). The compound under test is administered subcutaneously from the 2nd day following the hysterectomy. The luteal period is observed by the vaginal smear test. The compound is administered each day until the first oestrus begins. The compound is regarded as effective if the first oestrus begins within 5 days.], 16-(3-trifluoromethylphenoxy)-17,18,19,20-tetranor-trans and cis-$\Delta^3$-PGF$_{2\alpha}$ methyl ester, 16-(3-chlorophenoxy)-17,18,19,20-tetranor-trans and cis-$\Delta^3$-PGF$_{2\alpha}$ methyl ester and 16-phenoxy-17,18,19,20-tetranor-trans and cis-$\Delta^3$-PGF$_{2\alpha}$ methyl ester produce 66.7%, 60.0% and 85.7% luteolytic effect, respectively, at the daily doses of 0.5, 0.2 and 0.2 $\mu$g/kg animal body weight, respectively, and (iv) 17-phenyl-18,19,20-trinor-trans and cis-$\Delta^3$-PGF$_{2\alpha}$ methyl ester, 16-(3-trifluoromethylphenoxy)-17,18,19,20-tetranor-trans and cis-$\Delta^3$-PGF$_{2\alpha}$ methyl ester, 16-(3-chlorophenoxy)-17,18,19,20-tetranor-trans and cis-$\Delta^3$-PGF$_{2\alpha}$ methyl ester, 16-phenoxy-17,18,19,20-tetranor-trans and cis-$\Delta^3$-PGF$_{2\alpha}$ methyl ester, trans and cis-$\Delta^3$-PGF$_{1\alpha}$, 16-(4-chlorophenoxy)-17,18,19,20-tetranor-trans and cis-$\Delta^3$-PGF$_{2\alpha}$ methyl ester, 16,16-dimethyl-trans and cis-$\Delta^3$-PGE$_1$ methyl ester, methyl 9$\alpha$,11$\alpha$,15$\alpha$-trihydroxy-16-phenoxy-17,18,19,20-tetranorprosta-trans-3,trans-5,trans-13-trienoate and methyl 9$\alpha$,11$\alpha$,15$\alpha$-trihydroxy-16-(3-chlorophenoxy)-17,18,19,20-tetranorprosta-trans-3,trans-5,trans-13-trienoate stimulate uterine contraction in the pregnant female rat when administered intravenously on the 20th day of gestation at the doses of 5–10, 2, 2, 1–2, 200, 2–5, 0.2, 2 and 2 $\mu$g/kg animal body weight, respectively.

The following Reference Examples and Examples illustrate the preparation of new prostaglandin analogues of the present invention. In them 'IR', 'NMR' and 'TLC' represent respectively 'Infrared absorption spectrum', 'Nuclear magnetic resonance spectrum' and 'Thin layer chromatography'. Where solvent ratios are specified in chromatographic separations, the ratios are by volume.

EXAMPLE 1

Methyl 9α,11α,15α-trihydroxy-16-(3-trifluoromethylphenoxy)-17,18,19,20-tetranorprosta-trans and cis-3,cis-5,trans-13-trienoate [or 16-(3-trifluoromethylphenoxy)-17,18,19,20-tetranor-trans and cis-$\Delta^3$-PGF$_{2\alpha}$ methyl ester]

To a solution of 160 mg of methyl 9α,11α,15α-trihydroxy-16-(3-trifluoromethylphenoxy)-17,18,19,20-tetranorprosta-trans-2,cis-5,trans-13-trienoate in 4 ml of methanol there were added 250 mg of anhydrous potassium carbonate and the mixture was stirred at room temperature for one hour. The reaction mixture was then poured into an aqueous solution of ammonium chloride and extracted with ethyl acetate. The extract was washed with an aqueous solution of sodium chloride, dried over magnesium sulphate and concentrated under reduced pressure. The residue was purified by column chromatography on silica gel using a mixture of benzene and ethyl acetate (2:1) as eluent to give 110 mg of the title compound having the following physical characteristics:

TLC (developing solvent, ethyl acetate): Rf=0.16;

IR (liquid film): ν; 3400, 1740, 1600, 1490, 1450, 1340, 800 cm$^{-1}$;

NMR (CDCl$_3$ solution): δ; 7.50–7.00 (4H, m), 6.15–5.30 (6H, m), 4.65–4.40 (1H, m), 4.27–3.80 (4H, m), 3.66 and 3.67 (3H, each s), 3.19 and 3.11 (2H, each d).

EXAMPLE 2

Methyl 9α,11α,15α-trihydroxy-16-(3-chlorophenoxy)-17,18,19,20-tetranorprosta-trans and cis-3,cis-5,trans-13-trienoate [or 16-(3-chlorophenoxy)-17,18,19,20-tetranor-trans and cis-$\Delta^3$-PGF$_{2\alpha}$ methyl ester]

To a solution of 100 mg of methyl 9α,11α,15α-trihydroxy-16-(3-chlorophenoxy)-17,18,19,20-tetranorprosta-trans-2,cis-5,trans-13-trienoate in 2 ml of methanol there were added 79 mg of anhydrous potassium carbonate and the mixture was stirred at 0° C. for 2 hours. The reaction mixture was then poured into an aqueous solution of ammonium chloride and extracted with ethyl acetate. The extract was washed with an aqueous solution of sodium chloride, dried over magnesium sulphate and concentrated under reduced pressure. The residue was purified by column chromatography on silica gel using a mixture of cyclohexane and ethyl acetate (1:1) as eluent to give 75 mg of the title compound having the following physical characteristics:

TLC (developing solvent, chloroform-tetrahydrofuran-acetic acid=10:2:1): Rf=0.21;

IR (liquid film): ν; 3400, 2950, 1740, 1600, 1580, 1480, 1435, 980 cm$^{-1}$;

NMR (CDCl$_3$ solution): δ; 7.4–6.7 (4H, m), 6.7–5.2 (6H, m), 4.6–4.3 (1H, m), 4.3–4.05 (1H, m), 4.05–3.77 (3H, m), 3.66 and 3.67 (3H, each s), 3.11 and 3.19 (2H, each d); ultraviolet absorption (ethanol solution): λmax=230 mμ.

REFERENCE EXAMPLE 1

Methyl 9α-acetoxy-11α-(2-tetrahydropyranyloxy)-15α-hydroxy-17-phenyl-18,19,20-trinorprosta-cis-5,trans-13-dienoate To 20 ml of diethyl ether there were added 500 mg of magnesium and a small amount of iodine. The mixture was refluxed, 2.03 ml of 1-bromo-2-phenylethane were added dropwise to the mixture and the mixture was stirred for one hour with reflux.

To a solution of 2.08 g of 1α-acetoxy-2α-(6-methoxycarbonylhex-cis-2-enyl)-3β-(2-formyl-trans-vinyl)-4α-(2-tetrahydropyranyloxy)cyclopentane (prepared as described in Japanese Patent Publication No. 50-137961 or Belgian Patent Specification No. 827,803) in 40 ml of diethyl ether were added dropwise 17 ml of the ethereal solution obtained above at 0° C. and the mixture stirred at 0° C. for one hour. The reaction mixture was poured into an aqueous solution of ammonium chloride, extracted with ethyl acetate, washed with water and an aqueous solution of sodium chloride, dried over magnesium sulphate and concentrated under reduced pressure. The residue was purified by column chromatography on silica gel using a mixture of benzene and ethyl acetate (4:1) as eluent to give 770 mg of the title compound, 840 mg of its 15β-hydroxy epimer and 570 mg of their mixture. The title compound showed the following physical characteristics:

TLC (developing solvent, benzene-ethyl acetate=2:1): Rf=0.38, (15β-hydroxy epimer, Rf=0.48);

IR (liquid film): ν; 3450, 1740, 1610, 1490, 1250, 980, 760 cm$^{-1}$;

NMR (CDCl$_3$ solution): δ; 7.35 (5H, broad s), 5.85–5.00 (5H, m), 4.85–4.55 (1H, m), 3.70 (3H, s), 2.08 (3H, s).

REFERENCE EXAMPLE 2

Methyl 9α-acetoxy-11α,15α-bis(2-tetrahydropyranyloxy)-17-phenyl-18,19,20-trinorprosta-cis-5,trans-13-dienoate To a solution of 1.25 g of methyl 9α-acetoxy-11α-(2-tetrahydropyranyloxy)-15α-hydroxy-17-phenyl-18,19,20-trinorprosta-cis-5,trans-13-dienoate (prepared as described in Reference Example 1) in 20 ml of methylene chloride were added 0.52 ml of 2,3-dihydropyran and a catalytic amount of p-toluenesulphonic acid. The mixture was stirred at room temperature for 30 minutes, and then neutralized with an aqueous solution of sodium bicarbonate. The reaction mixture was diluted with ethyl acetate, washed with water and an aqueous solution of sodium chloride, dried over sodium sulphate and concentrated under reduced pressure. The residue was purified by column chromatography on silica gel using a mixture of benzene and ethyl acetate (9:1) as eluent to give 1.37 g of the title compound having the following physical characteristics:

TLC (developing solvent, benzene-ethyl acetate=2:1): Rf=0.73;

IR (liquid film): ν; 1740, 1500, 1250, 1030, 980, 760 cm$^{-1}$;

NMR (CDCl$_3$ solution): δ; 7.32 (5H, broad s), 5.85–5.00 (5H, m), 4.95–4.55 (2H, m), 3.68 (3H, s), 2.07 (3H, s).

REFERENCE EXAMPLE 3

Methyl 9α-hydroxy-11α,15α-bis(2-tetrahydropyranyloxy)-17-phenyl-18,19,20-trinorprosta-cis-5,trans-13-dienoate To a solution of 1.36 g of methyl 9α-acetoxy-11α,15α-bis(2-tetrahydropyranyloxy)-17-phenyl-18,19,20-trinorprosta-cis-5,trans-13-dienoate (prepared as described in Reference Example 2) in 18 ml of methanol were added 460 mg of anhydrous potassium carbonate, and the mixture was stirred at 40° C. for 2.5 hours. The reaction mixture was then neutralized with 1 N hydrochloric acid, diluted with ethyl acetate, washed with an aqueous solution of sodium bicarbonate and an aqueous solution of sodium chloride, dried over magnesium sulphate and concentrated under reduced pressure to give 1.12 g of the title compound having the following physical characteristics:

TLC (developing solvent, benzene-ethyl acetate=2:1): Rf=0.47;

IR (liquid film): ν; 3450, 1740, 1500, 1440, 1030, 980, 760 cm$^{-1}$;

NMR (CDCl$_3$ solution): δ; 7.40 (5H, s), 5.90–5.35 (4H, m), 4.95–4.65 (2H, m), 3.72 (3H, s).

REFERENCE EXAMPLE 4

Methyl 2-phenylseleno-9α-hydroxy-11α,15α-bis(2-tetrahydropyranyloxy)-17-phenyl-18,19,20-trinorprosta-cis-5,trans-13-dienoate To a solution of 0.67 ml of diisopropylamine in 15 ml of tetrahydrofuran were added dropwise 3.3 ml of a 1.4 M solution of n-butyllithium in n-hexane at −78° C., and the mixture was stirred at that temperature for 15 minutes to give a lithium diisopropylamide solution. To the lithium diisopropylamide solution was added dropwise a solution of 1.1 g of methyl 9α-hydroxy-11α,15α-bis(2-tetrahydropyranyloxy)-17-phenyl-18,19,20-trinorprosta-cis-5,trans-13-dienoate (prepared as described in Reference Example 3) in 2 ml of tetrahydrofuran at −78° C., and the mixture was stirred at the same temperature for 20 minutes. To the reaction mixture was added dropwise a solution of 930 mg of diphenyldiselenide in 3 ml of tetrahydrofuran at −78° C., and stirring was continued for one hour. The reaction mixture was then poured into an aqueous solution of ammonium chloride, and extracted with ethyl acetate. The extract was washed with water, 1 N hydrochloric acid, an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (5:1) as eluent to give 1.13 g of the title compound having the following physical characteristics:

TLC (developing solvent, benzene-ethyl acetate=2:1): Rf=0.56;

IR (liquid film): ν; 3450, 1735, 1580, 1440, 1030, 980, 750 cm$^{-1}$;

NMR (CDCl$_3$ solution): δ; 7.90–7.00 (10H, m), 5.75–5.15 (4H, m), 4.90–4.55 (2H, m), 3.62 (3H, s).

EXAMPLE 3

Methyl 9α-hydroxy-11α,15α-bis(2-tetrahydropyranyloxy)-17-phenyl-18,19,20-trinorprosta-trans-2,cis-5,trans-13-trienoate To a solution of 1.1 g of methyl 2-phenylseleno-9α-hydroxy-11α,15α-bis(2-tetrahydropyranyloxy)-17-phenyl-18,19,20-trinorprosta-cis-5,trans-13-dienoate (prepared as described in Reference Example 4) in 15 ml of a mixture of ethyl acetate and tetrahydrofuran (2:1) were added 0.8 ml of 30% hydrogen peroxide, and the mixture was stirred at 30° C. for 40 minutes. The reaction mixture was poured into water, washed with an aqueous solution of sodium carbonate, water and an aqueous solution of sodium chloride, dried over magnesium sulphate and concentrated under reduced pressure to give 960 mg of the title compound having the following physical characteristics:

TLC (developing solvent, benzene-ethyl acetate=2:1): Rf=0.47;

IR (liquid film): ν; 3450, 1735, 1650, 1500, 1030, 980, 760 cm$^{-1}$;

NMR (CDCl$_3$ solution): δ; 7.50–6.75 (6H, m), 6.10–5.30 (5H, m), 4.90–4.60 (2H, m), 3.72 (3H, s).

EXAMPLE 4

Methyl 9α,11α,15α-trihydroxy-17-phenyl-18,19,20-trinorprosta-trans-2,cis-5,trans-13-trienoate [or 17-phenyl-18,19,20-trinor-trans-Δ$^2$-PGF$_{2α}$ methyl ester]

To a solution of 250 mg of methyl 9α-hydroxy-11α,15α-bis(2-tetrahydropyranyloxy)-17-phenyl-18,19,20-trinorprosta-trans-2,cis-5,trans-13-trienoate (prepared as described in Example 3) in 4 ml of tetrahydrofuran were added 1.5 ml of 1 N hydrochloric acid, and the mixture was stirred at 40° C. for one hour. The reaction mixture was then poured into water, extracted with ethyl acetate, and the extract was washed with water and an aqueous solution of sodium chloride, dried over magnesium sulphate and concentrated under reduced pressure. The residue was purified by column chromatography on silica gel using a mixture of ethyl acetate and cyclohexane (1:1) as eluent to give 130 mg of the title compound having the following physical characteristics:

TLC (developing solvent, ethyl acetate): Rf=0.18;

IR (liquid film): ν; 3400, 1730, 1660, 1500, 1050, 980, 750 cm$^{-1}$;

NMR (CDCl$_3$ solution): δ; 5.70–5.20 (4H, m), 4.20–3.80 (3H, m), 3.68 (3H, s).

EXAMPLE 5

Methyl 9α,11α,15α-trihydroxy-17-phenyl-18,19,20-trinorprosta-trans and cis-3,cis-5,trans-13-trienoate [or 17-phenyl-18,19,20-trinor-trans and cis-Δ$^3$-PGF$_{2α}$ methyl ester]

By proceeding as described in Example 1 but replacing the methyl 9α,11α,15α-trihydroxy-16-(3-trifluoromethylphenoxy)-17,18,19,20-tetranorprosta-trans-2,cis-5,trans-13-trienoate by 50 mg of methyl 9α,11α,15α-trihydroxy-17-phenyl-18,19,20-trinorprosta-trans-2,cis-5,trans-13-trienoate (prepared as described in Example 4) dissolved in 1.5 ml of methanol and utilizing 85 mg of anhydrous potassium carbonate there were obtained 33 mg of the title compound having the following physical characteristics:

TLC (developing solvent, ethyl acetate): Rf=0.18;

IR (liquid film): $\nu$; 3400, 1740, 1640, 1500, 1440, 1250, 980, 750 cm$^{-1}$;

NMR (CDCl$_3$ solution): $\delta$; 7.40–7.00 (5H, m), 6.10–5.30 (6H, m), 4.20–3.80 (3H, m), 3.64 and 3.65 (3H, each s), 3.05 and 3.16 (2H, each d).

EXAMPLE 6

Methyl 9$\alpha$,11$\alpha$,15$\alpha$-trihydroxy-16-(3-trifluoromethylphenoxy)-17,18,19,20-tetranorprosta-trans and cis-3,cis-5,trans-13-trienoate [or 16-(3-trifluoromethylphenoxy)-17,18,19,20-tetranor-trans and cis-$\Delta^3$-PGF$_{2\alpha}$ methyl ester]

Under an atmosphere of nitrogen, 0.27 ml of a 1.4 M solution of n-butyllithium in n-hexane was added dropwise to a solution of 37.7 mg of diisopropylamine in 1 ml of tetrahydrofuran at $-20°$ C. and the mixture was stirred at the same temperature for 15 minutes to give lithium diisopropylamide. To the lithium diisopropylamide solution was added a solution of 73.2 mg of hexamethylphosphoramide in 1 ml of tetrahydrofuran at $-70°$ C. and the mixture was stirred at the same temperature for 30 minutes. To the resulting solution was added dropwise a solution of 40 mg of methyl 9$\alpha$,11$\alpha$,15$\alpha$-trihydroxy-16-(3-trifluoromethylphenoxy)-17,18,19,20-tetranorprosta-trans-2,cis-5 trans-13-trienoate in 2 ml of tetrahydrofuran at $-70°$ C., and the mixture was stirred at the same temperature for 2 hours and then concentrated under reduced pressure. The residue was diluted with 100 ml of diethyl ether, washed with water and an aqueous solution of sodium chloride, dried over magnesium sulphate and concentrated under reduced pressure. The residue was purified by column chromatography on silica gel using a mixture of benzene and ethyl acetate (2:1) as eluent to give 32 mg of the title compound having the same physical characteristics as those of the product of Example 1.

EXAMPLE 7

Methyl 9$\alpha$,11$\alpha$,15$\alpha$-trihydroxy-16-phenoxy-17,18,19,20-tetranorprosta-trans and cis-3,cis-5,trans-13-trienoate [or 16-phenoxy-17,18,19,20-tetranor-trans and cis-$\Delta^3$-PGF$_{2\alpha}$ methyl ester]

By proceeding as described in Example 2 but replacing the methyl 9$\alpha$,11$\alpha$,15$\alpha$-trihydroxy-16-(3-chlorophenoxy)-17,18,19,20-tetranorprosta-trans-2,cis-5,trans-13-trienoate by 165 mg of methyl 9$\alpha$,11$\alpha$,15$\alpha$-trihydroxy-16-phenoxy-17,18,19,20-tetranorprosta-trans-2,cis-5,trans-13-trienoate dissolved in 3 ml of methanol and utilizing 142 mg of potassium carbonate, there were obtained 141 mg of the title compound having the following physical characteristics:

TLC (developing solvent, ethyl acetate): Rf=0.28;

IR (liquid film): $\nu$; 3400, 2950, 1730, 1600, 1590, 1490, 980 cm$^{-1}$;

NMR (CDCl$_3$+D$_2$O solution): $\delta$; 7.4–6.7 (5H, m), 6.7–5.2 (6H, m), 4.7–4.3 (1H, m), 4.3–3.76 (4H, m), 3.67 and 3.66 (3H, each s), 3.3–2.9 (5H, m);

ultraviolet absorption (ethanol solution): $\lambda$max[$\epsilon$ max]; 205[17550], 223[27180], 234[23640], 271[1896], 277[1543] m$\mu$.

EXAMPLE 8

Methyl 9$\alpha$,11$\alpha$,15$\alpha$-trihydroxy-16-(4-chlorophenoxy)-17,18,19,20-tetranorprosta-trans and cis-3,cis-5,trans-13-trienoate [or 16-(4-chlorophenoxy)-17,18,19,20-tetranor-trans and cis-$\Delta^3$-PGF$_{2\alpha}$ methyl ester]

By proceeding as described in Example 2 but replacing the methyl 9$\alpha$,11$\alpha$,15$\alpha$-trihydroxy-16-(3-chlorophenoxy)-17,18,19,20-tetranorprosta-trans-2,cis-5,trans-13-trienoate by 32 mg of methyl 9$\alpha$,11$\alpha$,15$\alpha$-trihydroxy-16-(4-chlorophenoxy)-17,18,19,20-tetranorprosta-trans-2,cis-5,trans-13-trienoate dissolved in 2 ml of methanol and utilizing 30 mg of potassium carbonate, there were obtained 23 mg of the title compound having the following physical characteristics:

TLC (developing solvent, chloroform-tetrahydrofuran-acetic acid=10:2:1): Rf=0.22;

NMR (CDCl$_3$ solution): $\delta$; 7.40–7.05 (2H, m), 6.95–6.65 (2H, m), 6.63–5.10 (6H, m), 4.64–4.28 (1H, m), 4.25–4.02 (1H, m), 4.02–3.77 (3H, m), 3.67 and 3.66 (3H, each s), 3.19 and 3.11 (2H, each d).

EXAMPLE 9

Methyl 9$\alpha$,11$\alpha$,15$\alpha$-trihydroxy-16-(3-chlorophenoxy)-17,18,19,20-tetranorprosta-trans-3,cis-5,trans-13-trienoate [or 16-(3-chlorophenoxy)-17,18,19,20-tetranor-trans-$\Delta^3$-PGF$_{2\alpha}$ methyl ester] and methyl 9$\alpha$,11$\alpha$,15$\alpha$-trihydroxy-16-(3-chlorophenoxy)-17,18,19,20-tetranorprosta-cis-3,cis-5,trans-13-trienoate [or 16-(3-chlorphenoxy)-17,18,19,20-tetranor-cis-$\Delta^3$-PGF$_{2\alpha}$ methyl ester]

110 mg of methyl 9$\alpha$,11$\alpha$,15$\alpha$-trihydroxy-16-(3-chlorophenoxy)-17,18,19,20-tetranorprosta-trans and cis-3,cis-5,trans-13-trienoate (prepared as described in Example 2) were separated by thin layer chromatography on silica gel pre-treated with silver nitrate developing two times with a mixture of chloroform and methanol (first ratio 10:1, second ratio 5:1) as developing solvent to give 13 mg of the trans-$\Delta^3$-compound, 13 mg of the cis-$\Delta^3$-compound, and 35 mg of the starting material. The products showed the following physical characteristics:

(1) 16-(3-chlorophenoxy)-17,18,19,20-tetranor-trans-$\Delta^3$-PGF$_{2\alpha}$ methyl ester TLC (developing solvent, chloroform-methanol=5:1, using a silica gel plate pre-treated with AgNO$_3$, twice development): Rf=0.51;

NMR (CDCl$_3$ solution): $\delta$; 7.25–6.68 (4H, m), 6.68–5.20 (6H, m), 4.60–4.30 (1H, m), 4.25–4.00 (1H, m), 4.00–3.75 (3H, m), 3.654 (3H, s), 3.11 (2H, d);

ultraviolet absorption (ethanol solution): $\lambda$max-[$\epsilon$max]; 205[126400], 226[94000], 268[5730], 274[6990], 282[6060] m$\mu$.

(2) 16-(3-chlorophenoxy)-17,18,19,20-tetranor-cis-$\Delta^3$-PGF$_{2\alpha}$ methyl ester TLC (developing solvent, chloroform-methanol=5:1, using a silica gel plate pre-treated with AgNO$_3$, twice development): Rf=0.43;

NMR (CDCl$_3$ solution): $\delta$; 7.25–6.68 (4H, m), 6.68–5.20 (6H, m), 4.60–4.30 (1H, m), 4.30–3.75 (4H, m), 3.663 (3H, s), 3.19 (2H, d);

ultraviolet absorption (ethanol solution): λmax-[εmax]; 205[45480], 227[35800], 269[2230], 275[2880], 282[2622] mµ.

EXAMPLE 10

Methyl 9α,11α,15α-trihydroxy-16-phenoxy-17,18,19,20-tetranorprosta-trans-3,cis-5,trans-13-trienoate [or 16-phenoxy-17,18,19,20-tetranor-trans-$\Delta^3$-PGF$_{2\alpha}$ methyl ester] and methyl 9α,11α,15α-trihydroxy-16-phenoxy-17,18,19,20-tetranorprosta-cis-3,cis-5,trans-13-trienoate [or 16-phenoxy-17,18,19,20-tetranor-cis-$\Delta^3$-PGF$_{2\alpha}$ methyl ester]

28 mg of methyl 9α,11α,15α-trihydroxy-16-phenoxy-17,18,19,20-tetranorprosta-trans and cis-3,cis-5,trans-13-trienoate (prepared as described in Example 7; were separated by thin layer chromatography on silica gel pre-treated with silver nitrate developing three times with a mixture of chloroform and ethanol (5:1) as developing solvent to give 3 mg of the trans-$\Delta^3$-compound, 2 mg of the cis-$\Delta^3$-compound, and 13 mg of the starting material. The products showed the following physical characteristics:

(1) 16-phenoxy-17,18,19,20-tetranor-trans-$\Delta^3$-PGF$_{2\alpha}$ methyl ester TLC (developing solvent, chloroform-ethanol=5:1, using a silica gel plate pre-treated with AgNO$_3$, twice development): Rf=0.31;

NMR (CDCl$_3$ solution): δ; 7.500–7.045 (5H, m), 6.433 (1H, dd), 5.986 (1H, t), 5,909–5.227 (4H, m), 4.500 (1H, m), 4.318–3.636 (4H, m), 3.977 (2H, d), 3.659 (3H, s), 3.100 (2H, d), 2.886 (1H, m), 2.500–2.045 (4H, m), 1.818–1.363 (2H, m).

(2) 16-phenoxy-17,18,19,20-tetranor-cis-$\Delta^3$-PGF$_{2\alpha}$ methyl ester

TLC (developing solvent, chloroform-ethanol=5:1, using a silica gel plate pre-treated with AgNO$_3$, twice development): Rf=0.26;

NMR (CDCl$_3$ solution): δ; 7.500–7.045 (5H, m), 6.431 (1H, t), 6.168 (1H, t), 5.909–5.227 (4H, m), 4.500 (1H, m), 4.318–3.636 (4H, m), 3.977 (2H, d), 3.650 (3H, s), 3.190 (2H, d), 2.886 (1H, m), 2.500–2.045 (4H, m), 1.818–1.363 (2H, m).

REFERENCE EXAMPLE 5

9α,11α,15α-Tris(2-tetrahydropyranyloxy)prosta-trans-2,trans-13-dienoic acid

By proceeding as described in Reference Example 2, but replacing the methyl 9α-acetoxy-11α-(2-tetrahydropyranyloxy)-15α-hydroxy-17-phenyl-18,19,20-trinorprosta-cis-5,trans-13-dienoate by 9α,11α,15α-trihydroxyprosta-trans-2,trans-13-dienoic acid (prepared as described in our British Pat. No. 1416410), there was obtained the title compound having the following physical characteristics:

TLC (developing solvent, methylene chloride-methanol=20:1): Rf=0.21;

IR (liquid film): ν; 2940, 2860, 1720, 1695, 1655, 1200, 1130, 1075, 1020, 980, 870, 810 cm$^{-1}$;

NMR (CDCl$_3$ solution): δ; 8.83 (1H, broad s), 7.06 (1H, dt), 5.79 (1H, d), 5.68–5.20 (2H, m), 4.92–4.53 (3H, m), 4.38–3.20 (9H, m).

EXAMPLE 11

9α,11α,15α-Tris(2-tetrahydropyranyloxy)prosta-trans and cis-3,trans-13-dienoic acid By proceeding as described in Example 6, but replacing the methyl 9α,11α,15α-trihydroxy-16-(3-trifluoromethylphenoxy)-17,18,19,20-tetranorprosta-trans-2,cis-5,trans-13-trienoate by 872 mg of 9α,11α,15α-tris(2-tetrahydropyranyloxy)prosta-trans-2,trans-13-dienoic acid (prepared as described in Reference Example 5), there were obtained 275 mg of the title compound having the following physical characteristics:

TLC (developing solvent, methylene chloride-methanol=20:1): Rf=0.21;

IR (liquid film): ν; 2940, 2860, 1735, 1710, 1200, 1135, 1075, 1025, 980, 870, 815 cm$^{-1}$;

NMR (CDCl$_3$ solution): δ; 7.10 (1H, broad s), 5.83–5.14 (4H, m), 4.90–4.49 (3H, m), 4.90–3.26 (9H, m), 3.20–2.92 (2H, m).

EXAMPLE 12

9α,11α,15α-Trihydroxyprosta-trans and cis-3,trans-13-dienoic acid [or trans and cis-$\Delta^3$-PGF$_{1\alpha}$]

A solution of 322 mg of 9α,11α,15α-tris(2-tetrahydropyranyloxy)prosta-trans and cis-3,trans-13-dienoic acid (prepared as described in Example 11) in a mixture of 0.5 ml of tetrahydrofuran and 5 ml of 65% aqueous acetic acid was stirred at 45° C. for two hours, the reaction mixture was diluted with ethyl acetate, washed with water and an aqueous solution of sodium chloride, dried over sodium sulphate and concentrated under reduced pressure. The residue was purified by column chromatography on silica gel using a mixture of cyclohexane and ethyl acetate (1:2) as eluent to give 96 mg of the title compound having the following physical characteristics:

TLC (developing solvent, ethyl acetate-formic acid=400:5): Rf=0.18;

IR (liquid film): ν; 3320, 2940, 2860, 1710, 1460, 1405, 1210, 1120, 1030, 970 cm$^{-1}$;

NMR (CDCl$_3$+acetone−d$_6$ solution): δ; 5.84–5.23 (4H, m), 4.65 (4H, broad s), 4.32–3.70 (3H, m), 3.25–2.88 (2H, m).

EXAMPLE 13

Methyl 9α-hydroxy-11α,15α-bis(2-tetrahydropyranyloxy)-16,16-dimethylprosta-trans and cis-3,trans-13-dienoate By proceeding as described in Example 6, but replacing the methyl 9α,11α,15α-trihydroxy-16-(3-trifluoromethylphenoxy)-17,18,19,20-tetranorprosta-trans-2,cis-5,trans-13-trienoate by 470 mg of 9α-hydroxy-11α,15α-bis(2-tetrahydropyranyloxy)-16,16-dimethylprosta-trans-2,trans-13-dienoic acid (prepared as described in our U.S. patent application Ser. No. 646,316), there was obtained 9α-hydroxy-11α,15α-bis(2-tetrahydropyranyloxy)-16,16-dimethylprosta-trans and cis-3,trans-13-dienoic acid. To a solution of the 9α-hydroxy-11α,15α-bis(2-tetrahydropyranyloxy)-16,16-dimethylprosta-trans and cis-3,trans-13-dienoic acid obtained, in a mixture of ethyl acetate and diethyl ether, was added a freshly prepared ethereal solution of diazomethane at 0° C. until the reaction mixture turned pale yellow. The reaction mixture was concentrated under reduced pressure at a low temperature, and the residue was purified by column chromatography on silica gel using a mixture of benzene and ethyl acetate (4:1) as eluent to give 175 mg of the title compound having the following physical characteristics:

TLC (developing solvent, benzene-ethyl acetate=2:1): Rf=0.39;

IR (liquid film): $\nu$; 3450, 1740, 1440, 1020, 980 cm$^{-1}$;

NMR (CDCl$_3$ solution): $\delta$; 5.60–5.20 (4H, m), 4.70–4.43 (2H, m), 3.61 and 3.60 (3H, each s), 3.16–2.85 (2H, m).

EXAMPLE 14

Methyl 9-oxo-11α,15α-bis(2-tetrahydropyranyloxy)-16,16-dimethylprosta-trans and cis-3,trans-13-dienoate To a suspension of 208 mg of N-chlorosuccinimide in 6.5 ml of toluene were added 0.272 ml of dimethyl sulphide at −20° C., and the mixture was stirred for 1.5 hours at −20° C. To the solution was added a solution of 175 mg of methyl 9α-hydroxy-11α,15α-bis(2-tetrahydropyranyloxy)-16,16-dimethylprosta-trans and cis-3,trans-13-dienoate (prepared as described in Example 13) in 4 ml of toluene, and the mixture was stirred for two hours at −20° C. To the solution thus obtained was added a solution of 0.39 ml of triethylamine in 1 ml of n-pentane with stirring. Stirring was continued for 10 minutes at room temperature. The reaction mixture was extracted with ethyl acetate, and the extract was washed with water and an aqueous solution of sodium chloride, dried over magnesium sulphate and concentrated under reduced pressure. The residue was purified by column chromatography on silica gel using a mixture of benzene and ethyl acetate (9:1) as eluent to give 130 mg of the title compound having the following physical characteristics:

TLC (developing solvent, benzene-ethyl acetate=2:1): Rf=0.65;

IR (liquid film): $\nu$; 1740, 1710, 1440, 1040, 980 cm$^{-1}$;

NMR (CCl$_4$ solution): $\delta$; 5.80–5.35 (4H, m), 4.88–4.45 (2H, m), 3.63 (3H, s).

EXAMPLE 15

Methyl 9-oxo-11α,15α-dihydroxy-16,16-dimethylprosta-trans and cis-3,trans-13-dienoate [or 16,16-dimethyl-trans and cis-Δ$^3$-PGE$_1$ methyl ester]

By proceeding as described in Example 12, but replacing the 9α,11α,15α-tris(2-tetrahydropyranyloxy)-prosta-trans and cis-3,trans-13-dienoic acid by 130 mg of methyl 9-oxo-11α,15α-bis(2-tetrahydropyranyloxy)-16,16-dimethylprosta-trans and cis-3,trans-13-dienoate (prepared as described in Example 14), there were obtained 60 mg of the title compound having the following physical characteristics:

TLC (developing solvent, ethyl acetate): Rf=0.26;

IR (liquid film): $\nu$; 3450, 1740, 1440, 1160, 980 cm$^{-1}$;

P NMR (CDCl$_3$ solution): $\delta$; 5.90–5.35 (4H, m), 4.10–3.70 (2H, m), 3.65 (3H, s), 3.10–2.93 (2H, m), 2.87–2.55 (1H, m), 1.05–0.70 (9H, m).

REFERENCE EXAMPLE 6

2α-(6-Methoxycarbonylhex-trans-5-enyl)-3β-benzoyloxymethyl-4α-(2-tetrahydropyranyloxy)cyclopentan-1α-ol To a solution of 3.1 g of 2α-(6-methoxycarbonylhex-trans-5-enyl)-3β-hydroxymethyl-4α-(2-tetrahydropyranyloxy)cyclopentan-1α-ol (prepared as described hereafter) in a mixture of 30 ml of methylene chloride and 4.45 ml of pyridine was added dropwise over a period of one hour a solution of 1.4 ml of benzoyl chloride in 25 ml of methylene chloride at −25° to −20° C. with stirring. Stirring of the mixture was continued for 1 hour at the same temperature. The reaction mixture was quenched with an aqueous solution of sodium bicarbonate, and extracted with ethyl acetate. The extract was washed with cold 1 N hydrochloric acid, water and an aqueous solution of sodium chloride, dried over magnesium sulphate and concentrated under reduced pressure to give 4.1 g of the crude title compound having the following physical characteristic:

TLC (developing solvent, benzene-ethyl acetate=2:1): Rf=0.36.

2α-(6-Methoxycarbonylhex-trans-5-enyl)-3β-hydroxymethyl-4α-(2-tetrahydropyranloxy)cyclopentan-1α-ol used as a starting material in the above procedure, was prepared from 2α-(6-methoxycarbonylhex-cis-2-enyl)-3β-hydroxymethyl-4α-(2-tetrahydropyranyloxy)cyclopentan-1α-ol as follows:

(1)

2α-(6-methoxycarbonylhexyl)-3β-hydroxymethyl-4α-(2-tetrahydropyranyloxy)cyclopentan-1α-ol 14.2 g of 2α-(6-methoxycarbonylhex-cis-2-enyl)-3β-hydroxymethyl-4α-(2-tetrahydropyranyloxy)cyclopentan-1α-ol (prepared as described in Belgian Patent Specification No. 838,582) was hydrogenated at a pressure of one atmosphere in 300 ml of methanol containing 3 g of 5% (w/w) palladium on charcoal. The reduction was stopped after the absorption of one equivalent of hydrogen gas. The catalyst was removed by filtration and the filtrate was concentrated under reduced pressure to give 13.8 g of the title compound (1) having the following physical characteristics:

TLC (developing solvent, benzene-ethyl acetate=1:1): Rf=0.28;

IR (liquid film): $\nu$; 3450, 1740, 1440, 1030 cm$^{-1}$;

NMR (CDCl$_3$ solution): $\delta$; 5.00–4.55 (1H, m), 3.70 (3H, s), (2)

2α-(6-Phenylseleno-6-methoxycarbonylhexyl)-3β-hydroxymethyl-4α-(2-tetrahydropyranyloxy)cyclopentan-1α-ol Under an atmosphere of nitrogen, a solution of 19.4 ml of diisopropylamine in 350 ml of tetrahydrofuran was cooled to −78° C., and to it was added dropwise 114 ml of a 1.2 M solution of n-butyllithium in n-hexane and the mixture was stirred at −78° C. for 20 minutes to give lithium diisopropylamide. To the lithium diisopropylamide solution was added dropwise a solution of 13.8 g of 2α-(6-methoxycarbonylhexyl)-3β-hydroxymethyl-4α-(2-tetrahydropyranyloxy)cyclopentan-1α-ol [prepared as described in (1) above] in 100 ml of tetrahydrofuran at −78° C. and the mixture was stirred at the same temperature for 30 minutes. A solution of 18.2 g of diphenyldiselenide in 50 ml of tetrahydrofuran was added dropwise to the reaction mixture at −78° C. and the solution was stirred at the same temperature for one hour and then at 0° C. for 20 minutes. The reaction mixture was poured into an aqueous solution of ammonium chloride and extracted with ethyl acetate. The extract was washed with water and an aqueous solution of sodium chloride, dried over magnesium sulphate and concentrated under reduced pressure. The residue was purified by column chromatography on silica gel using a mixture of benzene and ethyl acetate (3:2) as eluent to give 15.8 g of the title compound (2) having the following physical characteristics:

TLC (developing solvent, benzene-ethyl acetate=1:1): Rf=0.37;
IR (liquid film): ν; 3450, 1740, 1580, 1440, 1030 cm$^{-1}$;
NMR (CDCl$_3$ solution): δ; 7.75–7.10 (5H, m), 5.00–4.55 (1H, m), 3.70 (3H, s).

(3)
2α-(6-Methoxycarbonylhex-trans-5-enyl)-3β-hydroxymethyl-4α-(2-tetrahydropyranyloxy)cyclopentan-1αol To a solution of 15.8 g of 2α-(6-phenylseleno-6-methoxycarbonylhexyl)-3β-hydroxymethyl-4α-(2-tetrahydropyranyloxy)cyclopentan-1α-ol [prepared as described in (2) above] in a mixture of 200 ml of ethyl acetate and 100 ml of tetrahydrofuran, there were added 4.5 g of sodium carbonate and 6.2 ml of 30% hydrogen peroxide and the mixture was stirred at 30° C. for 30 minutes. The reaction mixture was then poured into water, washed with an aqueous solution of sodium carbonate, water and an aqueous solution of sodium chloride, dried over magnesium sulphate and concentrated under reduced pressure to give 10.4 g of the title compound (3) having the following physical characteristics:

TLC (developing solvent, benzene-ethyl acetate=1:1): Rf=0.28;
IR (liquid film): ν; 3450, 1735, 1660, 1440, 1030 cm$^{-1}$;
NMR (CDCl$_3$ solution): δ; 6.90 (1H, dt), 5.82 (1H, d), 5.00–4.55 (1H, m), 3.70 (3H, s).

REFERENCE EXAMPLE 7

1α,4α-Bis(2-tetrahydropyranyloxy)-2α-(6-methoxycarbonylhex-trans-5-enyl)-3β-benzoyloxymethylcyclopentane By proceeding as described in Reference Example 2, but replacing the methyl 9α-acetoxy-11α-(2-tetrahydropyranyloxy)-15α-hydroxy-17-phenyl-18,19,20-trinorprosta-cis-5,trans-13-dienoate by 4.1 g of 2α-(6-methoxycarbonylhex-trans-5-enyl)-3β-benzoyloxymethyl-4α-(2-tetrahydroyranyloxy)cyclopentan-1α-ol (prepared as described in Reference Example 6), there were obtained 5.0 g of the crude title compound having the following physical characteristic:

TLC (developing solvent, benzene-ethyl acetate=2:1): Rf=0.73.

REFERENCE EXAMPLE 8

1α,4α-Bis(2-tetrahydropyranyloxy)-2α-(6-carboxyhex-trans-5-enyl)-3β-hydroxymethylcyclopentane A solution of 5.0 g of 1α,4α-bis(2-tetrahydropyranyloxy)-2α-(6-methoxycarbonylhex-trans-5-enyl)-3β-benzoyloxymethylcyclopentane (prepared as described in Reference Example 7) in 35 ml of ethanol was stirred with 40 ml of a 5% (w/v) aqueous potassium hydroxide solution at 50° C. for 1.5 hours. The reaction mixture was acidified to pH 3 to 4 with an aqueous solution of oxalic acid, extracted with ethyl acetate, and the extract was washed with water and an aqueous solution of sodium chloride, dried over magnesium sulphate and concentrated under reduced pressure. The residue was purified by column chromatography on silica gel using a mixture of benzene and ethyl acetate (2:1) as eluent to give 2.8 g of the title compound having the following physical characteristics:

TLC (developing solvent, chloroform-tetrahydrofuran-acetic acid=10:2:1): Rf=0.54;
IR (liquid film): ν; 1730–1700, 1020 cm$^{-1}$;
NMR (CDCl$_3$ solution): δ; 7.30–6.65 (3H, m), 5.82 (1H, d), 4.92–4.50 (2H, m).

REFERENCE EXAMPLE 9

1α,4α-Bis(2-tetrahydropyranyloxy)-2α-(6-methoxycarbonylhex-trans-5-enyl)-3β-hydroxymethylcyclopentane To a solution of 1.5 g of 1α,4α-bis(2-tetrahydropyranyloxy)-2α-(6-carboxyhex-trans-5-enyl)-3β-hydroxymethylcyclopentane (prepared as described in Reference Example 8) in a mixture of 25 ml of ethyl acetate and 25 ml of diethyl ether, was added a freshly prepared ethereal solution of diazomethane at 0° C. until the reaction mixture turned pale yellow. The reaction mixture was then concentrated under reduced pressure at a low temperature to give 1.53 g of the crude title compound having the following physical characteristic:

TLC (developing solvent, benzene-ethyl acetate=1:1): Rf=0.40.

REFERENCE EXAMPLE 10

1α,4α-Bis(2-tetrahydropyranyloxy)-2α-(6-methoxycarbonylhex-trans-5-enyl)-3β-formylcyclopentane Under an atmosphere of nitrogen, 4.2 g of chromium trioxide were added to a solution of 6.65 ml of pyridine in 100 ml of methylene chloride with stirring and the mixture was then stirred for 10 minutes at room temperature. 20 g of infusorial earth were added to the solution, and then there was added a solution of 1.53 g of 1α,4α-bis(2-tetrahydropyranyloxy)-2α-(6-methoxycarbonylhex-trans-5-enyl)-3β-hydroxymethylcyclopentane (prepared as described in Reference Example 9) in 30 ml of methylene chloride at 10° C. After stirring for 10 minutes, 35 g of sodium bisulphate monohydrate were added to the reaction mixture and stirring was continued for a further 15 minutes. The resulting precipitate was filtered off using a pad of magnesium sulphate and the filtrate was concentrated under reduced pressure. The residue was purified by column chromatography on silica gel using a mixture of benzene and ethyl acetate (5:1) as eluent to give 1.09 g of the title compound having the following physical characteristics:

TLC (developing solvent, benzene-ethyl acetate=2:1): Rf=0.66;
IR (liquid film): ν; 1730, 1660, 1440, 1240, 1020 cm$^{-1}$;
NMR (CDCl$_3$ solution): δ; 9.90–9.72 (1H, m), 6.94 (1H, dt), 5.82 (1H, d), 4.92–4.50 (2H, m), 3.70 (3H, s).

REFERENCE EXAMPLE 11

Methyl 9α,11α-bis(2-tetrahydropyranyloxy)-15-oxo-16-phenoxy-17,18,19,20-tetranorprosta-trans-2,trans-13-dienoate Under an atmosphere of nitrogen, a solution of 940 mg of dimethyl 2-oxo-3-phenoxypropylphosphonate in 3 ml of anhydrous tetrahydrofuran were added dropwise to a suspension of 114 mg of sodium hydride (63% content) in 20 ml of anhydrous tetrahydrofuran at room temperature, and the mixture was stirred at that temperature until a clear solution was obtained. To the solution was added a solution of 930 mg of 1α,4α-bis(2-tetrahydropyranyloxy)-2α-(6-methoxycarbonylhex-trans-5-enyl)-3β-formylcyclopentane (prepared as described in Reference Example 10) in 3 ml of anhydrous tetrahydrofuran, and the mixture was stirred at room temperature for 30 minutes and then at 60° to 65° C. for 2 hours. The reaction mixture was then neutralized with acetic acid, filtered through a pad of silica gel, and the filtrate was concentrated under reduced pressure. The residue was purified by column chromatography on silica gel using a mixture of benzene and ethyl acetate (5:1) as eluent to give 850 mg of the title compound having the following physical characteristics:

IR (liquid film): ν; 1730, 1690, 1600, 1500, 1140, 1030, 980 cm$^{-1}$;

NMR (CDCl$_3$ solution): δ; 7.45–6.30 (8H, m), 5.82 (1H, d), 4.90–4.40 (4H, m), 3.70 (3H, s).

REFERENCE EXAMPLE 12

Methyl 9α,11α-bis(2-tetrahydropyranyloxy)-15ε-hydroxy-16-phenoxy-17,18,19,20-tetranorprosta-trans-2,trans-13-dienoate To a solution of 850 mg of methyl 9α,11α-bis(2-tetrahydropyranyloxy)-15-oxo-16-phenoxy-17,18,19,20-tetranorprosta-trans-2,trans-13-dienoate (prepared as described in Reference Example 11) in 12 ml of absolute methanol were added 190 mg of sodium borohydride at −40° to −50° C. and the mixture was stirred at the same temperature for 15 minutes. After quenching with acetic acid, the reaction mixture was concentrated under reduced pressure. The residue was dissolved in ethyl acetate, washed with an aqueous solution of sodium bicarbonate, water and an aqueous solution of sodium chloride, dried over magnesium sulphate and concentrated under reduced pressue to give 850 mg of the crude title compound having the following physical characteristics:

TLC (developing solvent, benzene-ethyl acetate=2:1): Rf=0.47 and 0.51;

NMR (CDCl$_3$ solution): δ; 7.50–6.65 (6H, m), 5.92–5.50 (3H, m), 4.90–4.35 (3H, m), 3.70 (3H, s).

EXAMPLE 16

Methyl 9α,11α-bis(2-tetrahydropyranyloxy)-15ε-hydroxy-16-phenoxy-17,18,19,20-tetranorprosta-trans and cis-3,trans-13-dienoate By proceeding as described in Example 6, but replacing the methyl 9α,11α,15α-trihydroxy-16-(3-trifluoromethylphenoxy)-17,18,19,20-tetranorprosta-trans-2,cis-5,trans-13-trienoate by 368 mg of methyl 9α,11α-bis(2-tetrahydropyranyloxy)-15ε-hydroxy-16-phenoxy-17,18,19,20-tetranorprosta-trans-2,trans-13-dienoate (prepared as described in Reference Example 12), there were obtained 210 mg of the title compound having the following physical characteristic:

NMR (CDCl$_3$ solution): δ; 7.52–6.70 (5H, m), 5.95–5.40 (4H, m), 4.85–4.30 (3H, m), 3.66 (3H, s).

EXAMPLE 17

Methyl 9α,11α,15α-trihydroxy-16-phenoxy-17,18,19,20-tetranorprosta-trans and cis-3,trans-13-dienoate [or 16-phenoxy-17,18,19,20-tetranor-trans and cis-Δ$^3$-PGF$_{1α}$ methyl ester]

By proceeding as described in Example 12, but replacing the 9α,11α,15α-tris(2-tetrahydropyranyloxy)-prosta-trans and cis-3,trans-13-dienoic acid by 177 mg of methyl 9α,11α-bis(2-tetrahydropyranyloxy)-15ε-hydroxy-16-phenoxy-17,18,19,20-tetranorprosta-trans and cis-3,trans-13-dienoate (prepared as described in Example 16), there were obtained 41 mg of the title compound, 30 mg of its 15β-hydroxy isomer and 10 mg of their mixture. The title compound showed the following physical characteristics:

TLC (developing solvent, ethyl acetate): Rf=0.13 (15β-hydroxy isomer, Rf=0.18);

IR (liquid film): ν; 3400, 1740, 1600, 1590, 1500, 1250, 980, 760 cm$^{-1}$;

NMR (CDCl$_3$ solution): δ; 7.38–6.80 (5H, m), 5.72–5.40 (4H, m), 4.58–4.34 (1H, m), 4.27–3.80 (4H, m), 3.65 and 3.64 (3H, each s), 3.12–2.90 (2H, m).

EXAMPLE 18

Methyl 9α,11α,15α-tris(2-tetrahydropyranyloxy)-16-phenoxy-17,18,19,20-tetranorprosta-trans and cis-3,cis-5,trans-13-trienoate By proceeding as described in Reference Example 2, but replacing the methyl 9α-acetoxy-11α-(2-tetrahydropyranyloxy)-15α-hydroxy-17-phenyl-18,19,20-trinorprosta-cis-5,trans-13-dienoate by 43 mg of methyl 9α,11α,15α-trihydroxy-16-phenoxy-17,18,19,20-tetranorprosta-trans and cis-3,cis-5,trans-13-trienoate (prepared as described in Example 7), there were obtained 70 mg of the title compound having the following physical characteristic:

TLC (developing solvent, benzene-ethyl acetate=2:1): Rf=0.63.

EXAMPLE 19

Methyl 9α,11α,15α-trihydroxy-16-phenoxy-17,18,19,20-tetranorprosta-trans-3,trans-5,trans-13-trienoate A solution of 70 mg of methyl 9α,11α,15α-tris(2-tetrahydropyranyloxy)-16-phenoxy-17,18,19,20-tetranorprosta-trans and cis-3,cis-5,trans-13-trienoate (prepared as described in Example 18) in 2 ml of carbon tetrachloride was treated with 0.012 ml of a 0.1 N solution of iodine in carbon tetrachloride. The reaction mixture was allowed to stand in a glass-stoppered Pyrex flask exposed to ordinary diffuse laboratory light at room temperature for 25 hours, and the solvent was then evaporated by a stream of nitrogen to give methyl 9α,11α,15α-tris(2-tetrahydropyranyloxy)-16-phenoxy-17,18,19,20-tetranorprosta-trans-3,trans-5,trans-13-trienoate. The compound thus obtained was dissolved in 2 ml of methanol, and a small amount of p-toluenesulphonic acid was added. The reaction mixture was stirred at 40° C. for 30 minutes, diluted with diethyl ether, washed with an aqueous solution of sodium chloride, dried over sodium sulphate and concentrated under reduced pressure. The residue was purified by column chromatography on silica gel using a mixture of benzene and ethyl acetate (1:2) as eluent to give 14.4 mg of the title compound having the following physical characteristics:

TLC (developing solvent, chloroform-ethanol=5:1): Rf=0.42;

IR (CHCl$_3$ solution): ν; 3420, 3020, 1733, 1601, 1589, 1454, 1244, 1040, 992, 974 cm$^{-1}$;

NMR (CDCl$_3$ solution): δ; 7.4–7.1 (2H, m), 7.1–6.8 (3H, m), 6.4–5.2 (6H, m), 4.47 (1H, m), 4.12 (1H, m), 3.91 (2H, m), 3.65 (3H, s).

EXAMPLE 20

Methyl 9α,11α,15α-tris(2-tetrahydropyranyloxy)-16-(3-chlorophenoxy)-17,18,19,20-tetranorprosta-trans and cis-3,cis-5,trans-13-trienoate By proceeding as described in Reference Example 2, but replacing the methyl 9α-acetoxy-11α-(2-tetrahydropyranyloxy)-15α-hydroxy-17-phenyl-18,19,20-trinorprosta-cis-5,trans-13-dienoate by 52 mg of methyl 9α,11α,15α-trihydroxy-16-(3-chlorophenoxy)-17,18,19,20-tetranorprosta-trans and cis-3,cis-5,trans-13-trienoate (prepared as described in Example 2), there were obtained 82 mg of the title compound having the following physical characteristic:

TLC (developing solvent, benzene-ethyl acetate=2:1): Rf=0.58.

EXAMPLE 21

Methyl 9α,11α,15α-trihydroxy-16-(3-chlorophenoxy)-17,18,19,20-tetranorprosta-trans-3,trans-5,trans-13-trienoate By proceeding as described in Example 19, but replacing the methyl 9α,11α,15α-tris(2-tetrahydropyranyloxy)-16-phenoxy-17,18,19,20-tetranorprosta-trans and cis-3,cis-5,trans-13-trienoate by 82 mg of methyl 9α,11α,15α-tris(2-tetrahydropyranyloxy)-16-(3-chlorophenoxy)-17,18,19,20-tetranorprosta-trans and cis-3,cis-5,trans-13-trienoate (prepared as described in Example 20), there were obtained 28 mg of the title compound having the following physical characteristics:

TLC (developing solvent, chloroform-ethanol=5:1): Rf=0.36;

IR (CHCl$_3$ solution): ν; 3400, 3020, 1731, 1596, 1582, 1476, 997, 976 cm$^{-1}$;

NMR (CDCl$_3$ solution): δ; 7.4–6.7 (4H, m), 6.4–5.2 (6H, m), 4.45 (1H, m), 4.14 (1H, m), 3.9 (2H, m), 3.66 (3H, d).

EXAMPLE 22

β-Cyclodextrin clathrate of methyl 9α,11α,15α-trihydroxy-16-(3-chlorophenoxy)-17,18,19,20-tetranorprosta-trans and cis-3,cis-5,trans-13-trienoate [or β-cyclodextrin clathrate of 16-(3-chlorophenoxy)-17,18,19,20-tetranor-trans and cis-Δ$^3$-PGF$_{2α}$ methyl ester]

A solution of 3.39 mg of methyl 9α,11α,15α-trihydroxy-16-(3-chlorophenoxy)-17,18,19,20-tetranorprosta-trans and cis-3,cis-5,trans-13-trienoate (prepared as described in Example 2) in 1 ml of ethanol was added to a solution of 35.68 mg of β-cyclodextrin in 1.5 ml of water and the mixture was stirred at room temperature for 5 minutes. The mixture was concentrated under reduced pressure to give 39 mg of the β-cyclodextrin clathrate of the compound specified in the title. The content of prostaglandin analogue in the product was 8.68%.

The compounds used as starting materials in Examples 1, 2, 6, 7 and 8 may be prepared as described in our U.S. application Ser. No. 713,941 and our Dutch Application No. 76, 09134.

The present invention includes within its scope pharmaceutical compositions which comprise at least one new therapeutically useful compound of general formula VI, or cyclodextrin clathrate or non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult female the doses per person are generally between 0.001 and 50 mg by oral, intravaginal, intravenous and extra-amniotic administration for contraception and menstrual regulation and in the termination of pregnancy and the induction of labour in pregnant females. In domestic female mammals, such as cows, mares, sows, ewes and bitches, the doses are generally between 0.01 and 50 mg/animal by intramuscular, subcutaneous, intrauterine, intravaginal or intravenous administration for the synchronization of oestrus, treatment of impaired fertility and the induction of abortion and of labour.

The following Example illustrates pharmaceutical compositions according to the invention.

EXAMPLE 23

Methyl 9α,11α,15α-trihydroxy-16-(3-chlorophenoxy)-17,18,19,20-tetranorprosta-trans and cis-3,cis-5,trans-13-trienote (2 mg) was dissolved in ethanol (10 ml), mixed with mannitol (18.5 g), sieved through a 30-mesh sieve, dried at 30° C. for 90 minutes and again sieved through a 30-mesh sieve. Aerosil (microfine silica, 200 mg) was added and the powder obtained was machine filled into one hundred No. 2 hard gelatin capsules to give capsules each containing 20 μg of methyl 9α,11α,15α-trihydroxy-16-(3-chlorophenoxy)-17,18,19,20-tetranorprosta-trans and cis-3,cis-5,trans-13-trienoate which after swallowing of the capsule is released into the stomach.

What we claim is:

1. Prostaglandin analogues of the general formula:

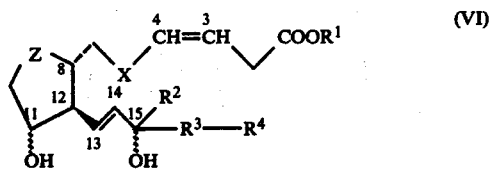

wherein X represents ethylene, Z represents

$R^1$ represents a hydrogen atom or a straight- or branched-chain alkyl group containing from 1 to 12 carbon atoms, $R^2$ represents a hydrogen atom or a methyl group, $R^3$ and $R^4$ together represent a straight- or branched-chain alkyl group containing from 1 to 10 carbon atoms, and the double bond between $C_3$-$C_4$ is trans or cis, or trans and cis, and the double bond between $C_{13}$-$C_{14}$ is trans and cyclodextrin clathrates of such acids and esters, and when $R^1$ represents a hydrogen atom, non-toxic salts thereof.

2. Prostaglandin analogues according to claim 1 wherein $R^1$ represents a hydrogen atom or a straight- or branched-chain alkyl group containing from 1 to 4 carbon atoms.

3. Prostaglandin analogues according to claim 2 wherein $R^1$ represents a hydrogen atom or a methyl group.

4. Prostaglandin analogues according to claim 1 wherein $R^2$ represents a hydrogen atom.

5. Prostaglandin analgoues according to claim 1 wherein $R^3$ and $R^4$ together represent a pentyl group or a 1,1-dimethylpentyl group.

6. Prostaglandin analogues according to claim 1 wherein the hydroxy groups depicted in formula VI in claim 1 α- or β-configuration are attached to the carbon atom in α-configuration.

7. A compound according to claim 1 which is methyl 9-oxo-11α-dihydroxy-16,16-dimethylprosta-trans and cis-3, trans-13-dienoate.

* * * * *